United States Patent
Pesach et al.

(10) Patent No.: US 9,220,837 B2
(45) Date of Patent: Dec. 29, 2015

(54) METHOD AND DEVICE FOR DRUG DELIVERY

(75) Inventors: Benny Pesach, Rosh-Ha'ayin (IL); Ron Nagar, Tel Aviv (IL); Gabriel Bitton, Jerusalem (IL); Ram Weiss, Haifa (IL)

(73) Assignee: INSULINE MEDICAL LTD., Petach-Tikva (IL)

( * ) Notice: Subject to any disclaimer, the term of this patent is extended or adjusted under 35 U.S.C. 154(b) by 1035 days.

(21) Appl. No.: 11/821,230

(22) Filed: Jun. 21, 2007

(65) Prior Publication Data
US 2008/0281297 A1    Nov. 13, 2008

Related U.S. Application Data

(60) Provisional application No. 60/895,518, filed on Mar. 19, 2007, provisional application No. 60/895,519, filed on Mar. 19, 2007, provisional application No. 60/912,698, filed on Apr. 19, 2007, provisional application No. 60/940,721, filed on May 30, 2007.

(51) Int. Cl.
*A61M 5/142*    (2006.01)
*A61M 5/158*    (2006.01)
(Continued)

(52) U.S. Cl.
CPC ............ *A61M 5/14244* (2013.01); *A61M 5/158* (2013.01); *A61M 5/16831* (2013.01); *A61M 5/1723* (2013.01); *A61M 5/20* (2013.01); *A61B 18/08* (2013.01); *A61B 18/14* (2013.01); *A61B 18/1477* (2013.01); *A61B 18/1492* (2013.01); *A61B 18/18* (2013.01); *A61B 18/20* (2013.01); *A61B 2018/1425* (2013.01); *A61F 7/007* (2013.01); *A61M 5/1413* (2013.01);
(Continued)

(58) Field of Classification Search
CPC .................... A61M 37/0092; A61M 5/14244; A61M 5/158; A61M 5/1723
USPC ................... 604/65–67, 113, 175, 180, 890.1
See application file for complete search history.

(56) References Cited

U.S. PATENT DOCUMENTS 3,620,209 A    11/1971  Kravitz
3,683,911 A *  8/1972  McCormick .................. 604/180
(Continued)

FOREIGN PATENT DOCUMENTS

EP              1752174 A1    2/2007
WO        WO-00/18339       4/2000
(Continued)

OTHER PUBLICATIONS

European Search Report for EP1315647 mailed Jul. 26, 2013.
(Continued)

*Primary Examiner* — Aarti B Berdichevsky
*Assistant Examiner* — Matthew A Engel
(74) *Attorney, Agent, or Firm* — Cooley LLP

(57)    ABSTRACT

A method and a device for a delivery of a chemical substance to the body of the patient are provided. The device includes an infusion catheter configured to be inserted into a tissue, a catheter securing element configured to be adhered to the skin of the patient and further configured to secure the infusion catheter to the skin, a drug delivery pump configured to infuse a drug into the infusion catheter for delivery to a drug infused region on the body of the patient, and a treatment element configured to apply a treatment to the drug infused region to improve pharmacodynamics of the drug during a period of delivery of the drug to the patient.

60 Claims, 11 Drawing Sheets

(51) Int. Cl.
  A61M 5/168 (2006.01)
  A61M 5/172 (2006.01)
  A61M 5/20 (2006.01)
  A61B 18/14 (2006.01)
  A61B 18/18 (2006.01)
  A61F 7/00 (2006.01)
  A61M 5/14 (2006.01)
  A61M 39/10 (2006.01)
  A61N 1/30 (2006.01)
  A61N 7/00 (2006.01)
  A61N 5/06 (2006.01)
  A61M 5/42 (2006.01)
  A61B 18/08 (2006.01)
  A61B 18/20 (2006.01)

(52) U.S. Cl.
  CPC ....... *A61M 5/422* (2013.01); *A61M 2005/1581* (2013.01); *A61M 2005/1726* (2013.01); *A61M 2039/1022* (2013.01); *A61M 2205/05* (2013.01); *A61M 2205/051* (2013.01); *A61M 2205/052* (2013.01); *A61M 2205/058* (2013.01); *A61M 2205/8206* (2013.01); *A61N 1/30* (2013.01); *A61N 7/00* (2013.01); *A61N 2005/0645* (2013.01)

(56) References Cited

U.S. PATENT DOCUMENTS

| | | | |
|---|---|---|---|
| 4,010,749 A * | 3/1977 | Shaw | 604/503 |
| 4,230,105 A | 10/1980 | Harwood | |
| H71 H | 6/1986 | Sorenson et al. | |
| 4,628,928 A | 12/1986 | Lowell | |
| 4,685,911 A | 8/1987 | Konno et al. | |
| 4,744,787 A | 5/1988 | Phipps et al. | |
| 4,747,819 A | 5/1988 | Phipps et al. | |
| 4,771,772 A | 9/1988 | DeWitt | |
| 4,898,592 A | 2/1990 | Latzke et al. | |
| 4,948,587 A | 8/1990 | Kost et al. | |
| 4,963,360 A | 10/1990 | Argaud | |
| 4,987,897 A | 1/1991 | Funke | |
| 4,998,930 A | 3/1991 | Lundahl | |
| 5,047,007 A | 9/1991 | McNichols et al. | |
| 5,053,033 A | 10/1991 | Clarke | |
| 5,098,429 A | 3/1992 | Sterzer | |
| 5,113,859 A | 5/1992 | Funke | |
| 5,135,477 A | 8/1992 | Untereker et al. | |
| 5,213,568 A | 5/1993 | Lattin et al. | |
| 5,222,362 A * | 6/1993 | Maus et al. | 60/527 |
| 5,243,986 A | 9/1993 | Wurster | |
| 5,271,736 A | 12/1993 | Picha | |
| 5,306,252 A * | 4/1994 | Yutori et al. | 600/585 |
| 5,307,816 A | 5/1994 | Hashimoto et al. | |
| 5,324,521 A | 6/1994 | Gertner et al. | |
| 5,332,577 A | 7/1994 | Gertner et al. | |
| 5,354,324 A | 10/1994 | Gregory | |
| 5,378,475 A | 1/1995 | Smith et al. | |
| 5,383,873 A | 1/1995 | Hoey et al. | |
| 5,411,550 A | 5/1995 | Herweck et al. | |
| 5,430,016 A | 7/1995 | Balschmidt et al. | |
| 5,498,254 A | 3/1996 | Hoey et al. | |
| 5,512,048 A | 4/1996 | Slettenmark | |
| 5,523,092 A | 6/1996 | Hanson et al. | |
| 5,525,356 A | 6/1996 | Jevne et al. | |
| 5,527,292 A | 6/1996 | Adams et al. | |
| 5,545,208 A | 8/1996 | Wolff et al. | |
| 5,556,421 A | 9/1996 | Prutchi et al. | |
| 5,564,439 A | 10/1996 | Picha | |
| 5,567,592 A | 10/1996 | Benet et al. | |
| 5,571,152 A | 11/1996 | Chen et al. | |
| 5,590,657 A | 1/1997 | Cain et al. | |
| 5,591,445 A | 1/1997 | Hoey et al. | |
| 5,634,468 A | 6/1997 | Platt et al. | |
| 5,658,583 A | 8/1997 | Zhang | |
| 5,706,807 A | 1/1998 | Picha | |
| 5,713,847 A | 2/1998 | Howard, III et al. | |
| 5,725,017 A | 3/1998 | Elsberry et al. | |
| 5,725,567 A | 3/1998 | Wolff et al. | |
| 5,730,125 A | 3/1998 | Prutchi et al. | |
| 5,741,211 A | 4/1998 | Renirie et al. | |
| 5,798,065 A | 8/1998 | Picha | |
| 5,843,051 A | 12/1998 | Adams et al. | |
| 5,851,217 A | 12/1998 | Wolff et al. | |
| 5,851,231 A | 12/1998 | Wolff et al. | |
| 5,871,446 A | 2/1999 | Wilk | |
| 5,871,535 A | 2/1999 | Wolff et al. | |
| 5,882,332 A | 3/1999 | Wijay | |
| 5,919,216 A | 7/1999 | Houben et al. | |
| 5,919,479 A | 7/1999 | Zhang et al. | |
| 5,997,468 A | 12/1999 | Wolff et al. | |
| 6,004,346 A | 12/1999 | Wolff et al. | |
| 6,004,927 A | 12/1999 | Benet et al. | |
| 6,026,316 A | 2/2000 | Kucharczyk et al. | |
| 6,028,054 A | 2/2000 | Benet et al. | |
| 6,043,273 A | 3/2000 | Duhaylongsod | |
| 6,060,454 A | 5/2000 | Duhaylongsod | |
| 6,061,587 A | 5/2000 | Kucharczyk et al. | |
| 6,087,394 A | 7/2000 | Duhaylongsod | |
| 6,093,167 A | 7/2000 | Houben et al. | |
| 6,101,412 A | 8/2000 | Duhaylongsod | |
| 6,122,536 A | 9/2000 | Sun et al. | |
| 6,125,290 A | 9/2000 | Miesel | |
| 6,125,291 A | 9/2000 | Miesel et al. | |
| 6,127,117 A | 10/2000 | Morris et al. | |
| 6,127,410 A | 10/2000 | Duhaylongsod | |
| 6,133,242 A | 10/2000 | Zalewski et al. | |
| 6,134,459 A | 10/2000 | Roberts et al. | |
| 6,135,978 A | 10/2000 | Houben et al. | |
| 6,141,589 A | 10/2000 | Duhaylongsod | |
| 6,144,866 A | 11/2000 | Miesel et al. | |
| 6,152,898 A | 11/2000 | Olsen | |
| 6,156,029 A | 12/2000 | Mueller | |
| 6,161,047 A | 12/2000 | King et al. | |
| 6,198,952 B1 | 3/2001 | Miesel | |
| 6,198,966 B1 | 3/2001 | Heruth | |
| 6,210,368 B1 | 4/2001 | Rogers | |
| 6,228,050 B1 | 5/2001 | Olsen et al. | |
| 6,228,595 B1 | 5/2001 | Morris et al. | |
| 6,238,367 B1 | 5/2001 | Christiansen et al. | |
| 6,245,347 B1 | 6/2001 | Zhang | |
| 6,247,812 B1 | 6/2001 | Miehle et al. | |
| 6,254,598 B1 | 7/2001 | Edwards et al. | |
| 6,261,280 B1 | 7/2001 | Houben et al. | |
| 6,261,595 B1 | 7/2001 | Stanley | |
| 6,269,340 B1 | 7/2001 | Ford et al. | |
| 6,283,949 B1 | 9/2001 | Roorda | |
| 6,284,266 B1 | 9/2001 | Zhang et al. | |
| 6,292,702 B1 | 9/2001 | King et al. | |
| 6,296,630 B1 | 10/2001 | Altman et al. | |
| 6,303,142 B1 | 10/2001 | Zhang | |
| 6,305,381 B1 | 10/2001 | Weijand et al. | |
| 6,306,431 B1 | 10/2001 | Zhang | |
| 6,312,412 B1 | 11/2001 | Saied et al. | |
| 6,323,184 B1 | 11/2001 | Zalewski et al. | |
| 6,338,850 B1 | 1/2002 | Jevnikar et al. | |
| 6,340,472 B1 | 1/2002 | Zhang | |
| 6,342,250 B1 | 1/2002 | Masters | |
| 6,375,628 B1 | 4/2002 | Zadno-Azizi et al. | |
| 6,377,846 B1 | 4/2002 | Chornenky et al. | |
| 6,379,382 B1 | 4/2002 | Yang | |
| 6,385,491 B1 | 5/2002 | Lindemans et al. | |
| 6,389,313 B1 | 5/2002 | Marchitto et al. | |
| 6,395,015 B1 | 5/2002 | Borst et al. | |
| 6,414,018 B1 | 7/2002 | Duhaylongsod | |
| 6,416,510 B1 | 7/2002 | Altman et al. | |
| 6,424,847 B1 | 7/2002 | Mastrototaro | |
| 6,425,853 B1 | 7/2002 | Edwards | |
| 6,427,088 B1 | 7/2002 | Bowman, IV et al. | |
| 6,442,435 B2 | 8/2002 | King et al. | |
| 6,447,443 B1 | 9/2002 | Keogh et al. | |
| 6,449,507 B1 | 9/2002 | Hill et al. | |
| 6,453,195 B1 | 9/2002 | Thompson | |
| 6,453,648 B1 | 9/2002 | Zhang et al. | |

(56) References Cited

U.S. PATENT DOCUMENTS

| | | |
|---|---|---|
| 6,456,883 B1 | 9/2002 | Torgerson et al. |
| 6,458,102 B1 | 10/2002 | Mann et al. |
| 6,458,118 B1 | 10/2002 | Lent et al. |
| 6,461,329 B1 * | 10/2002 | Van Antwerp et al. ....... 604/111 |
| 6,465,006 B1 | 10/2002 | Zhang et al. |
| 6,471,675 B1 | 10/2002 | Rogers et al. |
| 6,471,689 B1 | 10/2002 | Joseph et al. |
| 6,482,214 B1 | 11/2002 | Sidor, Jr. et al. |
| 6,485,464 B1 | 11/2002 | Christenson et al. |
| 6,487,446 B1 | 11/2002 | Hill et al. |
| 6,488,959 B2 | 12/2002 | Stanley et al. |
| 6,511,428 B1 | 1/2003 | Azuma et al. |
| 6,512,958 B1 | 1/2003 | Swoyer et al. |
| 6,528,086 B2 | 3/2003 | Zhang |
| 6,532,388 B1 | 3/2003 | Hill et al. |
| 6,537,242 B1 | 3/2003 | Palmer |
| 6,542,350 B1 | 4/2003 | Rogers |
| 6,544,212 B2 | 4/2003 | Galley et al. |
| 6,546,281 B1 | 4/2003 | Zhang et al. |
| 6,551,276 B1 | 4/2003 | Mann et al. |
| 6,551,346 B2 | 4/2003 | Crossley |
| 6,554,798 B1 | 4/2003 | Mann et al. |
| 6,558,345 B1 | 5/2003 | Houben et al. |
| 6,558,382 B2 | 5/2003 | Jahns et al. |
| 6,562,001 B2 | 5/2003 | Lebel et al. |
| 6,564,105 B2 | 5/2003 | Starkweather et al. |
| 6,571,125 B2 | 5/2003 | Thompson |
| 6,572,542 B1 | 6/2003 | Houben et al. |
| 6,572,583 B1 | 6/2003 | Olsen et al. |
| 6,577,899 B2 | 6/2003 | Lebel et al. |
| 6,584,335 B1 | 6/2003 | Haar et al. |
| 6,584,360 B2 | 6/2003 | Francischelli et al. |
| 6,585,644 B2 | 7/2003 | Lebel et al. |
| 6,585,707 B2 | 7/2003 | Cabiri et al. |
| 6,592,519 B1 | 7/2003 | Martinez |
| 6,597,946 B2 | 7/2003 | Avrahami et al. |
| 6,605,039 B2 | 8/2003 | Houben et al. |
| 6,613,082 B2 | 9/2003 | Yang |
| 6,613,084 B2 | 9/2003 | Yang |
| 6,613,350 B1 | 9/2003 | Zhang et al. |
| 6,615,083 B2 | 9/2003 | Kupper |
| 6,620,151 B2 | 9/2003 | Blischak et al. |
| 6,622,731 B2 | 9/2003 | Daniel et al. |
| 6,626,867 B1 | 9/2003 | Christenson et al. |
| 6,628,987 B1 | 9/2003 | Hill et al. |
| 6,628,989 B1 | 9/2003 | Penner et al. |
| 6,635,167 B1 | 10/2003 | Batman et al. |
| 6,644,321 B1 | 11/2003 | Behm |
| 6,645,176 B1 | 11/2003 | Christenson et al. |
| 6,647,299 B2 | 11/2003 | Bourget |
| 6,648,821 B2 | 11/2003 | Lebel et al. |
| 6,650,935 B1 | 11/2003 | Watmough |
| 6,659,948 B2 | 12/2003 | Lebel et al. |
| 6,669,663 B1 | 12/2003 | Thompson |
| 6,673,070 B2 | 1/2004 | Edwards et al. |
| 6,673,596 B1 | 1/2004 | Sayler et al. |
| 6,675,049 B2 | 1/2004 | Thompson et al. |
| 6,681,135 B1 | 1/2004 | Davis et al. |
| 6,685,452 B2 | 2/2004 | Christiansen et al. |
| 6,687,546 B2 | 2/2004 | Lebel et al. |
| 6,690,973 B2 | 2/2004 | Hill et al. |
| 6,694,191 B2 | 2/2004 | Starkweather et al. |
| 6,697,667 B1 | 2/2004 | Lee et al. |
| 6,706,038 B2 | 3/2004 | Francischelli et al. |
| 6,711,436 B1 | 3/2004 | Duhaylongsod |
| 6,714,822 B2 | 3/2004 | King et al. |
| 6,716,178 B1 | 4/2004 | Kilpatrick et al. |
| 6,718,208 B2 | 4/2004 | Hill et al. |
| 6,723,087 B2 | 4/2004 | O'Neill et al. |
| 6,726,673 B1 | 4/2004 | Zhang et al. |
| 6,728,574 B2 | 4/2004 | Ujhelyi et al. |
| 6,733,446 B2 | 5/2004 | Lebel et al. |
| 6,733,474 B2 | 5/2004 | Kusleika |
| 6,733,476 B2 | 5/2004 | Christenson et al. |
| 6,733,500 B2 | 5/2004 | Kelley et al. |
| 6,735,471 B2 | 5/2004 | Hill et al. |
| 6,736,789 B1 | 5/2004 | Spickermann |
| 6,736,797 B1 | 5/2004 | Larsen et al. |
| 6,738,671 B2 | 5/2004 | Christophersom et al. |
| 6,740,075 B2 | 5/2004 | Lebel et al. |
| 6,743,204 B2 | 6/2004 | Christenson et al. |
| 6,743,227 B2 | 6/2004 | Seraj et al. |
| 6,744,350 B2 | 6/2004 | Blomquist |
| 6,748,653 B2 | 6/2004 | Lindemans et al. |
| 6,752,155 B2 | 6/2004 | Behm |
| 6,755,849 B1 | 6/2004 | Gowda et al. |
| 6,756,053 B2 | 6/2004 | Zhang et al. |
| 6,758,810 B2 | 7/2004 | Lebel et al. |
| 6,758,828 B2 | 7/2004 | Hammer et al. |
| 6,764,446 B2 | 7/2004 | Wolinsky et al. |
| 6,766,183 B2 | 7/2004 | Walsh et al. |
| 6,780,426 B2 | 8/2004 | Zhang et al. |
| 6,799,149 B2 | 9/2004 | Hartlaub |
| 6,804,558 B2 | 10/2004 | Haller et al. |
| 6,805,667 B2 | 10/2004 | Christopherson et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,823,213 B1 | 11/2004 | Norris et al. |
| 6,827,702 B2 | 12/2004 | Lebel et al. |
| 6,836,687 B2 | 12/2004 | Kelley et al. |
| 6,846,823 B2 | 1/2005 | Landau et al. |
| 6,852,104 B2 | 2/2005 | Blomquist |
| 6,852,694 B2 | 2/2005 | Van Antwerp et al. |
| 6,865,419 B2 | 3/2005 | Mulligan et al. |
| 6,866,678 B2 | 3/2005 | Shenderova et al. |
| 6,872,200 B2 | 3/2005 | Mann et al. |
| 6,873,268 B2 | 3/2005 | Lebel et al. |
| 6,878,529 B2 | 4/2005 | Harrow et al. |
| 6,887,238 B2 | 5/2005 | Jahns et al. |
| 6,904,318 B2 | 6/2005 | Hill et al. |
| 6,913,763 B2 | 7/2005 | Lerner |
| 6,915,157 B2 | 7/2005 | Bennett et al. |
| 6,922,585 B2 | 7/2005 | Zhou et al. |
| 6,923,784 B2 | 8/2005 | Stein |
| 6,925,393 B1 | 8/2005 | Kalatz et al. |
| 6,927,246 B2 | 8/2005 | Noronha et al. |
| 6,928,338 B1 | 8/2005 | Buchser et al. |
| 6,930,602 B2 | 8/2005 | Villaseca et al. |
| 6,936,029 B2 | 8/2005 | Mann et al. |
| 6,950,708 B2 | 9/2005 | Bowman, IV et al. |
| 6,955,661 B1 | 10/2005 | Herweck et al. |
| 6,955,819 B2 | 10/2005 | Zhang et al. |
| 6,958,705 B2 | 10/2005 | Lebel et al. |
| 6,961,448 B2 | 11/2005 | Nichols et al. |
| 6,962,584 B1 | 11/2005 | Stone et al. |
| 6,966,322 B2 | 11/2005 | McVenes et al. |
| 6,969,369 B2 | 11/2005 | Struble |
| 6,974,437 B2 | 12/2005 | Lebel et al. |
| 6,978,174 B2 | 12/2005 | Gelfand et al. |
| 6,979,315 B2 | 12/2005 | Rogers et al. |
| 6,979,326 B2 | 12/2005 | Mann et al. |
| 6,979,351 B2 | 12/2005 | Forsell et al. |
| 6,984,229 B2 | 1/2006 | Neuberger |
| 6,985,768 B2 | 1/2006 | Hemming et al. |
| 6,991,916 B2 | 1/2006 | Benson et al. |
| 6,997,920 B2 | 2/2006 | Mann et al. |
| 7,011,630 B2 | 3/2006 | Desai et al. |
| 7,013,177 B1 | 3/2006 | Whitehurst et al. |
| 7,018,384 B2 | 3/2006 | Skakoon |
| 7,018,568 B2 | 3/2006 | Tierney |
| 7,024,236 B2 | 4/2006 | Ford et al. |
| 7,024,245 B2 | 4/2006 | Lebel et al. |
| 7,024,248 B2 | 4/2006 | Penner et al. |
| 7,025,743 B2 | 4/2006 | Mann et al. |
| 7,025,760 B2 | 4/2006 | Miller et al. |
| 7,027,856 B2 | 4/2006 | Zhou et al. |
| 7,027,871 B2 | 4/2006 | Burnes et al. |
| 7,033,338 B2 | 4/2006 | Vilks et al. |
| 7,041,704 B2 | 5/2006 | Burgard et al. |
| 7,044,082 B1 | 5/2006 | Hewett et al. |
| 7,052,483 B2 | 5/2006 | Wojcik |
| 7,054,782 B2 | 5/2006 | Hartlaub |

(56) References Cited

U.S. PATENT DOCUMENTS

| | | |
|---|---|---|
| 7,058,447 B2 | 6/2006 | Hill et al. |
| 7,063,684 B2 | 6/2006 | Moberg |
| 7,066,891 B2 | 6/2006 | Stadler et al. |
| 7,066,909 B1 | 6/2006 | Peter et al. |
| 7,069,078 B2 | 6/2006 | Houben |
| 7,072,802 B2 | 7/2006 | Hartlaub |
| 7,074,233 B1 | 7/2006 | Gowda et al. |
| 7,084,116 B2 | 8/2006 | Fraser et al. |
| 7,092,753 B2 | 8/2006 | Darvish et al. |
| 7,094,228 B2 | 8/2006 | Zhang et al. |
| 7,101,857 B2 | 9/2006 | Sung et al. |
| 7,107,086 B2 | 9/2006 | Reihl et al. |
| 7,107,093 B2 | 9/2006 | Burnes |
| 7,108,696 B2 | 9/2006 | Daniel et al. |
| 7,109,878 B2 | 9/2006 | Mann et al. |
| 7,115,606 B2 | 10/2006 | Landau et al. |
| 7,123,968 B1 | 10/2006 | Casscells, III et al. |
| 7,125,407 B2 | 10/2006 | Edwards et al. |
| 7,125,848 B2 | 10/2006 | Fraser et al. |
| 7,133,329 B2 | 11/2006 | Skyggebjerg et al. |
| 7,149,581 B2 | 12/2006 | Goedeke |
| 7,149,773 B2 | 12/2006 | Haller et al. |
| 7,150,975 B2 | 12/2006 | Tamada et al. |
| 7,151,961 B1 | 12/2006 | Whitehurst et al. |
| 7,160,252 B2 | 1/2007 | Cho et al. |
| 7,162,303 B2 | 1/2007 | Levin et al. |
| 7,162,307 B2 | 1/2007 | Patrias |
| 7,163,511 B2 | 1/2007 | Conn et al. |
| 7,164,948 B2 | 1/2007 | Struble et al. |
| 7,167,743 B2 | 1/2007 | Heruth et al. |
| 7,171,263 B2 | 1/2007 | Darvish et al. |
| 7,171,274 B2 | 1/2007 | Starkweather et al. |
| 7,179,226 B2 | 2/2007 | Crothall et al. |
| 7,181,505 B2 | 2/2007 | Haller et al. |
| 7,184,828 B2 | 2/2007 | Hill et al. |
| 7,184,829 B2 | 2/2007 | Hill et al. |
| 7,186,247 B2 | 3/2007 | Ujhelyi et al. |
| 7,187,979 B2 | 3/2007 | Haubrich et al. |
| 7,190,997 B1 | 3/2007 | Darvish et al. |
| 7,191,008 B2 | 3/2007 | Schmidt et al. |
| 7,193,521 B2 | 3/2007 | Moberg et al. |
| 7,203,541 B2 | 4/2007 | Sowelam et al. |
| 7,206,632 B2 | 4/2007 | King |
| 7,209,784 B2 | 4/2007 | Schmidt |
| 7,209,790 B2 | 4/2007 | Thompson et al. |
| 7,218,964 B2 | 5/2007 | Hill et al. |
| 2001/0022279 A1 | 9/2001 | Denyer et al. |
| 2001/0047195 A1 | 11/2001 | Crossley |
| 2002/0002326 A1 | 1/2002 | Causey et al. |
| 2002/0010406 A1 | 1/2002 | Douglas et al. |
| 2002/0026141 A1 | 2/2002 | Houben et al. |
| 2002/0032406 A1 | 3/2002 | Kusleika |
| 2002/0038101 A1 | 3/2002 | Avrahami et al. |
| 2002/0040208 A1* | 4/2002 | Flaherty et al. ......... 604/288.01 |
| 2002/0068869 A1 | 6/2002 | Brisken et al. |
| 2002/0072743 A1 | 6/2002 | KenKnight et al. |
| 2002/0077673 A1 | 6/2002 | Penner et al. |
| 2002/0082583 A1 | 6/2002 | Lerner |
| 2002/0082665 A1 | 6/2002 | Haller et al. |
| 2002/0102707 A1 | 8/2002 | Harrow et al. |
| 2002/0106410 A1 | 8/2002 | Masters |
| 2002/0133148 A1 | 9/2002 | Daniel et al. |
| 2002/0137014 A1 | 9/2002 | Anderson et al. |
| 2002/0176849 A1 | 11/2002 | Slepian |
| 2002/0177689 A1 | 11/2002 | Benson et al. |
| 2002/0177772 A1 | 11/2002 | Altman et al. |
| 2002/0177782 A1 | 11/2002 | Penner |
| 2002/0183682 A1 | 12/2002 | Darvish et al. |
| 2002/0183686 A1 | 12/2002 | Darvish et al. |
| 2003/0028089 A1 | 2/2003 | Galley et al. |
| 2003/0060765 A1 | 3/2003 | Campbell et al. |
| 2003/0069614 A1 | 4/2003 | Bowman et al. |
| 2003/0073609 A1 | 4/2003 | Pinkerton |
| 2003/0100885 A1 | 5/2003 | Pettis et al. |
| 2003/0130616 A1* | 7/2003 | Steil et al. ................ 604/66 |
| 2003/0138464 A1* | 7/2003 | Zhang et al. .................. 424/400 |
| 2003/0144712 A1 | 7/2003 | Streeter |
| 2003/0167033 A1 | 9/2003 | Chen et al. |
| 2003/0171401 A1 | 9/2003 | Johnson et al. |
| 2003/0176933 A1 | 9/2003 | Lebel et al. |
| 2003/0181852 A1 | 9/2003 | Mann et al. |
| 2003/0181894 A1 | 9/2003 | Neuberger |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0208152 A1 | 11/2003 | Avrahami et al. |
| 2003/0212364 A1 | 11/2003 | Mann et al. |
| 2003/0212441 A1 | 11/2003 | Starkweather et al. |
| 2004/0014131 A1 | 1/2004 | Benson et al. |
| 2004/0023844 A1 | 2/2004 | Pettis et al. |
| 2004/0024361 A1 | 2/2004 | Fago et al. |
| 2004/0028707 A1 | 2/2004 | Pinkerton |
| 2004/0030282 A1* | 2/2004 | Freyman et al. ............... 604/44 |
| 2004/0059328 A1 | 3/2004 | Daniel et al. |
| 2004/0062148 A1 | 4/2004 | Skyggebjerg et al. |
| 2004/0063200 A1 | 4/2004 | Chaikof et al. |
| 2004/0064086 A1 | 4/2004 | Gottlieb et al. |
| 2004/0064127 A1 | 4/2004 | Lerner |
| 2004/0064133 A1 | 4/2004 | Miller et al. |
| 2004/0073190 A1 | 4/2004 | Deem et al. |
| 2004/0082639 A1 | 4/2004 | Ho et al. |
| 2004/0085215 A1 | 5/2004 | Moberg et al. |
| 2004/0092885 A1 | 5/2004 | Duchon et al. |
| 2004/0098113 A1 | 5/2004 | Forsell et al. |
| 2004/0111132 A1 | 6/2004 | Shenderova et al. |
| 2004/0127895 A1 | 7/2004 | Flock et al. |
| 2004/0142034 A1 | 7/2004 | Thor et al. |
| 2004/0147872 A1 | 7/2004 | Thompson |
| 2004/0157884 A1 | 8/2004 | Johnson et al. |
| 2004/0171518 A1* | 9/2004 | Van Antwerp et al. ............ 514/3 |
| 2004/0186533 A1 | 9/2004 | Greenberg et al. |
| 2004/0193090 A1 | 9/2004 | Lebel et al. |
| 2004/0198822 A1 | 10/2004 | Fraser et al. |
| 2004/0202692 A1 | 10/2004 | Shanley et al. |
| 2004/0209869 A1 | 10/2004 | Landau et al. |
| 2004/0209960 A1 | 10/2004 | Burgard et al. |
| 2004/0210267 A1 | 10/2004 | Lebel et al. |
| 2004/0210280 A1* | 10/2004 | Liedtke ........................... 607/96 |
| 2004/0220551 A1* | 11/2004 | Flaherty et al. ............. 604/890.1 |
| 2004/0225338 A1 | 11/2004 | Lebel et al. |
| 2004/0230117 A1 | 11/2004 | Tosaya et al. |
| 2004/0236269 A1 | 11/2004 | Marchitto et al. |
| 2004/0248979 A1 | 12/2004 | Brettman et al. |
| 2004/0260239 A1 | 12/2004 | Kusleika |
| 2004/0265353 A1 | 12/2004 | Zhang et al. |
| 2005/0004663 A1 | 1/2005 | Llanos et al. |
| 2005/0008580 A1 | 1/2005 | Gong et al. |
| 2005/0009735 A1* | 1/2005 | Kim et al. ........................ 514/3 |
| 2005/0020577 A1 | 1/2005 | Landau et al. |
| 2005/0026909 A1 | 2/2005 | Landau et al. |
| 2005/0033231 A1 | 2/2005 | Powell |
| 2005/0033370 A1 | 2/2005 | Jelen et al. |
| 2005/0054725 A1 | 3/2005 | Thor et al. |
| 2005/0059938 A1 | 3/2005 | Malisch |
| 2005/0065464 A1 | 3/2005 | Talbot et al. |
| 2005/0065465 A1 | 3/2005 | Lebel et al. |
| 2005/0065556 A1 | 3/2005 | Reghabi et al. |
| 2005/0084477 A1 | 4/2005 | Van Antwerp et al. |
| 2005/0090866 A1 | 4/2005 | Miller et al. |
| 2005/0107353 A1 | 5/2005 | Burgard et al. |
| 2005/0107738 A1 | 5/2005 | Slater et al. |
| 2005/0107743 A1 | 5/2005 | Fangrow |
| 2005/0113798 A1 | 5/2005 | Slater et al. |
| 2005/0124560 A1 | 6/2005 | Sung et al. |
| 2005/0137670 A1 | 6/2005 | Christopherson et al. |
| 2005/0143636 A1 | 6/2005 | Zhang et al. |
| 2005/0148955 A1 | 7/2005 | Chong et al. |
| 2005/0171160 A1 | 8/2005 | Edgar et al. |
| 2005/0171513 A1 | 8/2005 | Mann et al. |
| 2005/0175665 A1 | 8/2005 | Hunter et al. |
| 2005/0175703 A1 | 8/2005 | Hunter et al. |
| 2005/0177201 A1 | 8/2005 | Freeman |
| 2005/0178395 A1 | 8/2005 | Hunter et al. |
| 2005/0178396 A1 | 8/2005 | Hunter et al. |

(56) References Cited

U.S. PATENT DOCUMENTS

| | | | |
|---|---|---|---|
| 2005/0182307 A1* | 8/2005 | Currie et al. .............. 600/300 |
| 2005/0182389 A1* | 8/2005 | LaPorte et al. ............ 604/890.1 |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/0192637 A1 | 9/2005 | Girouard et al. |
| 2005/0196421 A1 | 9/2005 | Hunter et al. |
| 2005/0197633 A1 | 9/2005 | Schwartz et al. |
| 2005/0208095 A1 | 9/2005 | Hunter et al. |
| 2005/0217674 A1 | 10/2005 | Burton et al. |
| 2005/0220836 A1 | 10/2005 | Falotico et al. |
| 2005/0221270 A1 | 10/2005 | Connelly et al. |
| 2005/0222191 A1 | 10/2005 | Falotico et al. |
| 2005/0228049 A1 | 10/2005 | Thor et al. |
| 2005/0229931 A1 | 10/2005 | Denyer et al. |
| 2005/0232964 A1 | 10/2005 | Fennimore |
| 2005/0232965 A1 | 10/2005 | Falotico |
| 2005/0239838 A1 | 10/2005 | Edgar et al. |
| 2005/0239890 A1 | 10/2005 | Fraser et al. |
| 2005/0245840 A1 | 11/2005 | Christopherson et al. |
| 2005/0249775 A1 | 11/2005 | Falotico et al. |
| 2005/0249776 A1 | 11/2005 | Chen et al. |
| 2005/0256165 A1 | 11/2005 | Edgar et al. |
| 2005/0256499 A1 | 11/2005 | Pettis et al. |
| 2005/0267550 A1 | 12/2005 | Hess et al. |
| 2005/0270245 A1 | 12/2005 | Villaseca et al. |
| 2005/0272719 A1 | 12/2005 | Landau et al. |
| 2005/0272806 A1 | 12/2005 | Falotico et al. |
| 2005/0276842 A1 | 12/2005 | Zhang et al. |
| 2005/0282799 A1 | 12/2005 | Landau et al. |
| 2005/0282859 A1 | 12/2005 | Thor |
| 2006/0025663 A1 | 2/2006 | Talbot et al. |
| 2006/0025756 A1 | 2/2006 | Francischelli et al. |
| 2006/0030837 A1 | 2/2006 | McKenna et al. |
| 2006/0030838 A1* | 2/2006 | Gonnelli .................... 604/890.1 |
| 2006/0031094 A1 | 2/2006 | Cohen et al. |
| 2006/0041243 A1 | 2/2006 | Nayak et al. |
| 2006/0063754 A1 | 3/2006 | Edgar et al. |
| 2006/0063755 A1 | 3/2006 | Edgar et al. |
| 2006/0063928 A1 | 3/2006 | Edgar et al. |
| 2006/0079858 A1 | 4/2006 | Miller et al. |
| 2006/0079941 A1 | 4/2006 | Ovsyshcher et al. |
| 2006/0094705 A1 | 5/2006 | Edgar et al. |
| 2006/0111704 A1 | 5/2006 | Brenneman et al. |
| 2006/0122666 A1 | 6/2006 | Nghiem et al. |
| 2006/0122863 A1 | 6/2006 | Gottesman et al. |
| 2006/0129050 A1 | 6/2006 | Martinson et al. |
| 2006/0129225 A1 | 6/2006 | Kopia et al. |
| 2006/0142819 A1 | 6/2006 | Penner et al. |
| 2006/0149218 A1 | 7/2006 | Slater et al. |
| 2006/0149339 A1 | 7/2006 | Burnes et al. |
| 2006/0173406 A1 | 8/2006 | Hayes et al. |
| 2006/0173444 A1 | 8/2006 | Choy et al. |
| 2006/0184092 A1 | 8/2006 | Atanasoska et al. |
| 2006/0184154 A1 | 8/2006 | Moberg et al. |
| 2006/0188575 A1 | 8/2006 | Thor et al. |
| 2006/0247311 A1 | 11/2006 | Fraser et al. |
| 2006/0253085 A1 | 11/2006 | Geismar et al. |
| 2006/0264509 A1 | 11/2006 | Fraser et al. |
| 2006/0264894 A1* | 11/2006 | Moberg et al. ................ 604/503 |
| 2006/0270968 A1 | 11/2006 | Greenberg et al. |
| 2006/0271020 A1* | 11/2006 | Huang et al. ............... 604/890.1 |
| 2006/0271112 A1 | 11/2006 | Martinson et al. |
| 2006/0272652 A1 | 12/2006 | Stocker et al. |
| 2006/0276542 A1 | 12/2006 | Fraser et al. |
| 2006/0293309 A1 | 12/2006 | Thor et al. |
| 2007/0003549 A1 | 1/2007 | Ignatovich et al. |
| 2007/0004752 A1 | 1/2007 | Coughlin et al. |
| 2007/0009956 A1 | 1/2007 | Srinivas et al. |
| 2007/0016163 A1 | 1/2007 | Santini et al. |
| 2007/0016170 A1 | 1/2007 | Kovelman |
| 2007/0026042 A1 | 2/2007 | Narayanan |
| 2007/0030764 A1 | 2/2007 | Skyggebjerg et al. |
| 2007/0033074 A1 | 2/2007 | Nitzan et al. |
| 2007/0038100 A1 | 2/2007 | Nita |
| 2007/0040449 A1 | 2/2007 | Spurlin et al. |
| 2007/0048350 A1 | 3/2007 | Falotico et al. |
| 2007/0051362 A1 | 3/2007 | Sullivan et al. |
| 2007/0053996 A1 | 3/2007 | Boyden et al. |
| 2007/0054319 A1 | 3/2007 | Boyden et al. |
| 2007/0054871 A1 | 3/2007 | Pastore et al. |
| 2007/0060652 A1 | 3/2007 | Fraser et al. |
| 2007/0060864 A1 | 3/2007 | Redding |
| 2007/0060871 A1 | 3/2007 | Istoc et al. |
| 2007/0083258 A1 | 4/2007 | Falotico et al. |
| 2007/0086952 A1 | 4/2007 | Steiner et al. |
| 2007/0087315 A1 | 4/2007 | Stuart et al. |
| 2007/0088248 A1 | 4/2007 | Glenn et al. |
| 2007/0093752 A1 | 4/2007 | Zhao et al. |
| 2007/0098753 A1 | 5/2007 | Falotico et al. |
| 2007/0112298 A1 | 5/2007 | Mueller et al. |
| 2008/0015624 A1 | 1/2008 | Sonoda et al. |
| 2008/0023593 A1 | 1/2008 | Ritota et al. |
| 2008/0200897 A1 | 8/2008 | Hoss et al. |
| 2008/0281297 A1 | 11/2008 | Pesach et al. |
| 2008/0319414 A1 | 12/2008 | Yodfat et al. |
| 2010/0057003 A1 | 3/2010 | Dos Santos |
| 2010/0106088 A1 | 4/2010 | Yodfat et al. |
| 2010/0152644 A1* | 6/2010 | Pesach et al. .................... 604/20 |
| 2010/0174225 A1 | 7/2010 | Pesach et al. |
| 2010/0286467 A1 | 11/2010 | Pesach et al. |
| 2010/0292557 A1 | 11/2010 | Pesach et al. |
| 2010/0318035 A1 | 12/2010 | Edwards et al. |
| 2011/0184342 A1 | 7/2011 | Pesach et al. |
| 2011/0288527 A1 | 11/2011 | Pesach et al. |

FOREIGN PATENT DOCUMENTS

| | | |
|---|---|---|
| WO | WO-00/78212 A1 | 12/2000 |
| WO | 02/28454 | 4/2002 |
| WO | 02/100386 | 12/2002 |
| WO | WO-2006/049570 A2 | 5/2006 |
| WO | WO-2006/091650 A2 | 8/2006 |
| WO | WO-2008/051924 A2 | 5/2008 |
| WO | WO-2008/114218 | 9/2008 |
| WO | WO-2008/114220 | 9/2008 |
| WO | WO-2008/114223 | 9/2008 |
| WO | WO-2008/114224 | 9/2008 |
| WO | WO-2009/081262 | 7/2009 |
| WO | WO-2010/052579 | 5/2010 |
| WO | 2011/016028 | 2/2011 |

OTHER PUBLICATIONS

Belinda et. al., (1996), Journal of Physiology, 572.3:811-820.
Bos et al., Biomaterials (2005), 26:3901-3909.
Clarke et. al., (2005), Diabetes Care, 28:2412-2417.
Facchinetti et. al., (2007), Journal of Diabetes Science and Technology, 1:617-623.
Heinemann, (2002), Diabetes Technology & Therapeutics, 5:673-682.
Koivisto et al. (1980), British Medical Journal, 280:1411-1413.
Koivisto et al., (1978), The New England Journal of Medicine, 298:79-83.
Magerl et. al., (1996), Journal of Physiology, 497:837-848.
Midttun et. al., (1996), Clinical Physiology, 16:259-274.
Rebrin et al., (2000), Diabetes Technology and Therapeutics, 2:461-472.
Shumaker et al., (2006), Lasers in Surgery and Medicine, 38:211-217.
Sindelka et al., (1994), Diabetologia, 37:377-380.

* cited by examiner

METHOD AND DEVICE FOR DRUG DELIVERY

CROSS REFERENCE TO RELATED APPLICATIONS

This application claims priority to U.S. Provisional Patent Application Ser. No. 60/895,518, filed Mar. 19, 2007, U.S. Provisional Patent Application Ser. No. 60/895,519, filed Mar. 19, 2007, U.S. Provisional Patent Application Ser. No. 60/912,698, filed Apr. 19, 2007 and U.S. Provisional Patent Application Ser. No. 60/940,721, filed May 30, 2007, each of which are incorporated by reference herein in its entirety.

BACKGROUND OF THE INVENTION

1. Field of the Invention

The present invention relates to systems and methods for delivering drugs to a patient. In particular, the present invention relates to systems and methods for subcutaneous infusion of drugs or substances and using energy sources to improve effectiveness of the infused drugs.

2. Background of the Invention

Diabetes is a very serious illness affecting millions of people today. Many diabetic patients require injection of insulin to maintain proper levels of glucose in their blood in order to survive. Such injections of insulin are done using drug delivery systems.

Many medical treatment systems and methods involve drug delivery systems that employ subcutaneous infusions of therapeutic fluids, drugs, proteins, and other compounds. Such delivery systems and methods, especially in the area of insulin delivery, have made use of subcutaneous catheters and continuous subcutaneous insulin infusion (CSII) pumps. In conventional insulin pumps, the pump is configured to be attached to a disposable thin plastic tube or a catheter through which insulin passes into the tissue. The catheter can be inserted transcutaneously, typically on the patient's abdomen and is changed every two to three days. New types of insulin pumps, such as the OmniPod pump manufactured by Insulet Corporation, do not have an external catheter and, instead, a catheter port that is embedded into the pump mechanism.

In many instances, the patients require insulin delivery around the clock to keep proper levels of glucose in their blood. Insulin can be delivered at a basal rate or in bolus doses. The basal rate represents insulin that is continuously delivered to the patient. Such continuous delivery of insulin keeps patient's blood glucose in the desired range between meals and over night. The bolus dose is an amount of insulin delivered to the patient matching a dose of carbohydrates consumed by the patient. When patient consumes food, his or her levels of glucose rise. Some conventional pump mechanisms are configured to react upon command, or by way of an algorithm, to the increase in glucose levels by delivering a bolus dose of insulin that matches the rise in the level of glucose and prevents large glucose excursions. However, many conventional subcutaneous drug delivery systems are incapable of quickly matching or preventing the rise of blood glucose. The delay in such matching is also true in case of the "rapid-acting" insulin. Some of the reasons for this delay include a lag in the absorption of insulin from the injection site and the time it takes for complex insulin molecules to break down into monomers.

Additionally, since blood glucose levels rise immediately following the meal, the delay in matching insulin to the rising levels causes post prandial hyperglycemic events (i.e., when levels of blood glucose are above normal) to occur. Further, occasionally after a certain period of time passes (e.g., 2-3 hours) after a meal, the blood glucose levels drop yet insulin concentrations in the blood rise followed by the peak of the systemic insulin effect and result in causing hypoglycemic events (i.e., when levels of blood glucose are below normal) to occur. Both hyperglycemic and hypoglycemic events are highly undesirable. Additionally, since the local blood perfusion at the insulin infusion region has large variations depending on the ambient temperature and other parameters, it induces large variations to said delay of the peak of time profile of the insulin action. Those variations in the insulin peak action period further increase the variability in the blood glucose level.

Thus, it is desirable to provide a system and a method that provides efficient and timely delivery of the drug to the patient. In particular, it is desirable to provide a system and a method for delivering insulin to the patient that improves effectiveness of insulin in the blood to maintain normal levels of blood glucose and prevent or reduce hyperglycemic and hypoglycemic events.

SUMMARY OF THE INVENTION

Embodiments of the present invention relate to systems, devices and methods for delivery of drugs, substances and/or chemicals (together "drugs" or "substances") to a patient and for improving the effectiveness of such drugs once they are delivered. In some embodiments of the present invention, a device for improving performance of catheter-based drug delivery devices is provided. The catheter can be an adjunct to a pump or embedded into the pump mechanism. In such embodiments, the device can be applied to a tissue region of the patient into which a drug (e.g., insulin) is delivered, to expose the tissue region to an energy source such as radiation, heat, mechanical vibrations, suction, massaging, acoustic stimulation (e.g., ultrasound), electrical stimulation, infusion of an additional substance(s), or any combination of the above to improve the drug's pharmacokinetic and/or pharmacodynamic profile.

Such a device, according to some embodiments of the present invention, can also be part of a catheter which has one section inside the tissue and another section that connects to a unit outside the tissue (i.e., a transcutaneous delivery system). As can be understood by one skilled in the art, properties (such as amplitude, phase, frequency, etc.) of the individual excitation source(s), the combination of excitation sources, the relative ratio and timing between the various excitation sources, may be controlled by a processor in order to achieve a desired response of the tissue region next to the catheter. The sources can also be adjusted according to the chemical/physical properties of the infused substance.

In some embodiments of the present invention, a device for supplying energy to a tissue region (or infused region) can be configured to monitor and control the properties of the excitation sources (such as amplitude, phase, intensity, frequency, etc.). Based on the monitoring, the information can be provided to a controller ("controller", also referred to as a "processing unit") that uses the information to reduce the variability of the drug delivery process. In such embodiments, the device can be configured to monitor properties of the tissue next to the catheter element (e.g., such as temperature). Based on such monitoring, the information can be provided to the controller that utilizes the information to improve the pharmacokinetic or pharmacodynamic profile of the drug in the desired direction as well as performance and reduce variability of the drug delivery process.

The device according to some embodiments of the present invention can be configured to either automatically detect the drug delivery through the catheter by the delivery apparatus, get a signal from the drug delivery device, get the signal from a separate button or switch to initiate a protocol of exposing the infused tissue region to the above described treatments or tissue stimulations. The device can then be configured to begin operating by applying a stimulation or a treatment to the tissue. The tissue response to the stimulation enhances the functionality of a drug delivery pump by enhancing the kinetics of molecule transport between the catheter tip placed inside the tissue to the various compartments of the tissue region around it and to the blood system.

In some embodiments, the applied treatment may reduce the variability of the drug absorption in the blood or lymph system and its local and systemic effects. For example, heating the tissue region in the vicinity of the area of drug delivery (i.e., infused region) to a preset regulated temperature during the drug infusion and absorption into the blood may make local blood perfusion at that region more reproducible and the drug absorption process more uniform and reproducible as well. Also, by reducing the delay between the drug delivery into the tissue and absorption into the blood system, the variability of the drug action induced by the delayed profile can be reduced. Optionally, the temperature of the region adjacent to the infusion region can be regulated for longer periods, but the cost may be the energy source volume and weight. Therefore, for minimization of the energy source size the heating period should be optimized in relation to the period of the drug infusion and absorption into the blood.

In some embodiments, the tissue treatment or stimulation device may be triggered manually by the user. The user may activate the treatment device or devices before or after the pump activation to enhance the tissue response to the delivered drug. In such embodiments, this can be done by pressing a button or a sequence of buttons on the tissue treatment device. In some embodiments, in case of communication between the drug delivery device and the treatment device, the treatment can be triggered manually by pressing a button or a sequence of buttons on the drug delivery device. For example, in case of an insulin pump, the pump may have a special button for triggering a "fast bolus" compared to the other bolus options provided by the pump. The fast insulin bolus mode can be configured to start one of the disclosed treatments in parallel to application of the insulin bolus infusion for a given period of time, such as 30 minutes (for example). This improves or modifies (in an advantageous manner) insulin's pharmacokinetics or pharmacodynamics, tissue blood perfusion and/or absorption in the blood and is highly attractive in conjunction with high glycemic index food. Application of a "fast bolus" may be useful in consumption of high glycemic index food where larger rapid glucose excursions occurs, but also in most of the cases of using insulin boluses for prandial coverage. Application of a "fast bolus" can be initiated by pressing a special sequence of buttons or choosing an optional bolus mode using the pump display and buttons. In some embodiments, the user may trigger the tissue treatment or stimulation before the application of the bolus to further improve the treatment effect. In some embodiments the user may trigger the tissue treatment or stimulation together with the infusion of the insulin bolus before the meal to further increase the treatment effect. In some embodiments the tissue treatment or stimulation may be triggered before the meal to increase the treatment effect. In some embodiments the tissue treatment or stimulation may be triggered after the bolus to save battery life.

In some embodiments, one effect of the treatments reduces local irritation caused by the infused drug and by that increases the infusion sets's durability and functionality period. For example, in case of insulin infusion, reducing the period in which the high concentration of insulin stays at the tissue, may reduce the irritation caused by insulin in some cases. Also increasing the local blood perfusion may support that and the longevity of the functionality of the infusion set.

Some embodiments of the present invention also provide methods for monitoring tissue parameters non-invasively or invasively using the catheter or both invasively and non-invasively, and using the information to control activation of the device of the present invention Some embodiments of the present invention also provide methods for improving or modifying a drug's pharmacokinetic or pharmacodynamic profile in order to reduce time to peak action in the blood of the injected material by applying a modulation pattern to the pump. With this modulation, the infusion fluid is slightly pulled in and out of the tissue during or after the drug infusion process. In such embodiments, this method may not require an addition of any other devices to the current infusion pump rather it can be configured to modulate drug flow from the drug delivery element or pump.

In some embodiments, a drug delivery pump may be mechanically or electronically connected to the catheter of the above-noted device embodiments. In such embodiments, the catheter unit includes at least one of the following excitation sources or at least one combination of two such sources from the following: a heat source (e.g., a heat resistor), a suction port activated by a pump (for example), a mechanical vibration source, an ultrasound excitation source, an ultrasound transducer, a light source, an optical fiber, a massaging element, and/or a combination of at least two of sources of heat, vibrations, suction, ultrasound, light and massaging.

In some embodiments, a device for drug delivery is provided which includes an infusion catheter for insertion into tissue, a drug delivery device for infusing the drug into and within the infusion catheter, a treatment device for applying a specific treatment or stimulation to the drug infused region in order to improve drug's pharmacokinetic, pharmacodynamic profile and/or to increase blood perfusion in that region during the drug delivery period to improve drug absorption into the blood system.

In some embodiments, a device for drug delivery is provided which includes an infusion catheter for insertion into tissue, a drug delivery device for infusing a drug into the infusion catheter, a treatment device for applying a specific treatment or stimulation to the drug infused region in order to improve, modify and/or stabilize the drug pharmacokinetics, pharmacodynamics, and/or to reduce variations of the drug absorption into the blood system.

In some embodiments, a device for drug delivery is provided and includes an infusion catheter for insertion into tissue, a drug delivery device for infusing a drug into the infusion catheter, a treatment device for applying a specific treatment or stimulation to the drug infused region to improve, modify and/or stabilize the drug's pharmacokinetics, pharmacodynamics and/or to reduce variations of the drug absorption process into the blood system, at least one sensor to measure the effect of the treatment device, and a control unit to control the operation of the treatment device using the information from the at least one sensor.

In some embodiments, a device for drug delivery is provided and includes an infusion catheter for insertion into tissue, a drug delivery device for infusing a drug into the infusion catheter, a sensor for detecting drug infusion through the catheter either directly or indirectly, a treatment device for applying a specific treatment to the drug infused region to improve, modify and/or stabilize the drug pharmacokinetics, pharmacodynamics and/or to reduce variations of the drug absorption process into the blood system, and a control unit for initiating a treatment profile with the treatment device after detection of the drug infusion with the sensor.

In some embodiments, a device for drug delivery is provided that includes an infusion catheter for insertion into tissue, a drug delivery device for infusing a drug into the infusion catheter, a housing for the drug delivery device, a sensor built into the housing to sense the operation of the infusion device upon a drug bolus being delivered by the device, a treatment element for applying a specific treatment to the drug infused region to improve, modify and/or to stabilize the drug pharmacokinetics or pharmacodynamics, an electronic control unit connected to the treatment element for initiating a treatment profile with the treatment element when the drug delivery device starts drug infusion. In some such embodiments, the unit is built into the housing.

In some embodiments, a device for drug delivery is provided that includes a drug delivery device, an infusion catheter for insertion into tissue. The infusion catheter is part of an infusion set including: an infusion catheter, a tube with or without connections that connects the infusion catheter to the drug delivery device, a treatment element for applying a specific treatment to the drug infused region of the tissue to improve, modify and/or stabilize the drug pharmacokinetics or pharmacodynamics, an adhesive element that is used to secure the treatment element and/or the infusion catheter to a position over the tissue, a communication channel between the drug delivery device and the treatment element, a control unit (i.e., a controller/processing unit) that initiates a treatment profile with the treatment element when the drug delivery device starts drug infusion. The elements of the device may be all or part contained in the same housing.

In some embodiments, a device for drug delivery is provided which includes a drug delivery device, and an infusion catheter for insertion into a tissue. The infusion catheter may be part of an infusion set including: an infusion catheter, a tube with or without connections that connects the infusion catheter to the drug delivery device, a treatment element for applying a specific treatment to the drug infused region of the tissue to improve, modify and/or stabilize the drug pharmacokinetics and/or pharmacodynamics, an adhesive element for securing the treatment element and/or the infusion catheter to a position over the tissue, a housing for the drug delivery device, a pickup coil or other sensor built into the housing to sense the operation of the infusion device when a bolus dose is delivered by the device, and a control unit that starts a treatment profile with the treatment element when the drug delivery device starts the drug infusion. The unit is built into the housing.

In some embodiments, a device for drug delivery is provided which includes an infusion catheter for insertion into tissue. The infusion catheter may be part of an infusion set including: an infusion catheter, a tube with or without connections that connects the infusion catheter to the drug delivery device, a treatment element for applying a specific treatment to the drug tissue infused region to improve, modify and/or stabilize the drug pharmacokinetics and/or pharmacodynamics, an adhesive element that is used to secure the treatment element and/or the infusion catheter to a position over the tissue, a housing for the drug delivery device, and a control unit that starts a treatment profile with the treatment element when the drug delivery device starts the drug infusion.

In some such embodiments, the adhesive, the treatment element and the infusion set are disposable while all other components are reusable. In some embodiments, the adhesive, the treatment element, the infusion set and the control unit are disposable while all other components are reusable. In some embodiments, all components including the infusion device and the power source (batteries) are disposable. The above elements of the device in the present invention such as the drug delivery device, the infusion catheter, the treatment device and others may be separate individual elements or elements contained all or part of them in one housing.

DETAILED DESCRIPTION OF THE INVENTION

Figure 1:
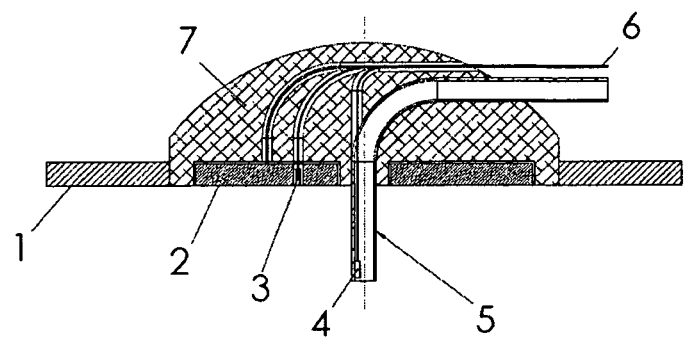
FIG. 1 illustrates an exemplary catheter for drug delivery combined with a heating element attached to the skin around the catheter, according to some embodiments of the present invention.

The present invention relates to devices for improving, modifying and/or stabilizing pharmacokinetic and/or pharmacodynamic profile of a drug infused into the tissue by a catheter and absorbed into the blood or lymphatic system. The devices described in some of the embodiments of the present application apply additional treatment or stimulation to the vicinity of the drug delivery site. The treatment can be one or combination of the following tissue treatment treatments modalities: heating, modifying temperature, massaging, mechanical vibration, acoustic vibration, ultrasound, suction, infusion of an additional substance or chemical, applying a low electric field, applying a low magnetic field, light irradiation, infrared ("RF") irradiation, microwave ("MW") irradiation, etc. In some embodiments, the device has a catheter for insertion within the tissue to infuse a substance into the infused tissue region. The infused tissue region (i.e., the infused region) can be one of the skin layers or the subcutaneous tissue or deeper tissue elements within any organ or viscera.

The catheter may also have a securing mechanical part that adheres to the skin and secures the catheter into its location and prevent it from being pulled out accidentally. The proximal end of the catheter may be connected to a drug delivery device which controls the infusion profile of the drug. In some embodiments, the drug delivery device also controls the additional treatment applied to the infused tissue region. In those embodiments, there is a communication channel between the drug delivery device and the treatment device. The communication can be either wired or wireless. Portions of the treatment device can be disposed inside the drug delivery device or outside of it. In some embodiments, the drug delivery device is a drug delivery pump, such as an insulin pump.

In some embodiments, the present invention is a device controlled by a pump that infuses a drug into a tissue region, which applies an additional treatment to the vicinity of the drug delivery site. In some embodiments, the pump's electronic processing unit operates based on a predetermined protocol or algorithm, any additional inputs and/or a drug-infusion profile of the applied treatment. In some embodiments, the pump's electronic processing unit communicates with the treatment device processing unit, which operates based on a predetermined protocol or algorithm and according to a drug infusion profile of the applied treatment. In some embodiments, the device regularly queries the pump's status using the pump's built-in communication capability. Based on the received data, the device operates in accordance with a predetermined protocol or algorithm of the applied treatment.

In some embodiments, the devices are neither controlled by the pump nor have any communications with the drug delivery pump. Instead, the devices detect the drug-delivery profile through the catheter and apply the treatment according to a predetermined protocol or algorithm. In such embodiments, the treatment device includes a sensor that can detect the drug infusion flow inside the catheter and deliver the information to the device processing unit, which operates based on a predetermined protocol or algorithm and on an infusion profile of the applied treatment. The drug flow can be detected by any conventional sensors, such as an optical sensor that detects the drug flow in a transparent catheter, a laser Doppler sensor, an ultrasonic Doppler sensor, a pressure sensor, a conductivity sensor, an inductance sensor that can measure changes in the flow rate of the infusion fluid optionally under induced magnetic field. In some embodiments, the drug flow sensor detects not only the existence of a drug infusion flow, but also the infusion rate and uses that information in the treatment algorithm. In some embodiments, the drug infusion sensor detects the electromagnetic or acoustic emission of the drug delivery pump motor or electronics. In some embodiments, the device senses some additional parameters of the tissue and uses that information as well in the treatment algorithm.

In some embodiments, tissue treatment controls the temperature of the tissue region into which the drug is delivered. In some embodiments, temperature control can be to set a profile of temperature rise in a known rate, temperature stabilization at a known period and ending the profile by returning to the natural tissue temperature. This profile can be induced by a heater that heats the drug infused tissue region. Other temperature profiles for treatment or excitation of the drug infused tissue region are possible as well. For example, a cooling profile for decreasing blood perfusion or to induce a specific pharmacokinetic and/or pharmacodynamic profile for the drug or heating for short time intervals to further improve drug pharmacokinetics or pharmacodynamics. In some embodiments, the temperature profile can be applied to a larger region than the drug infused tissue region. Doing so may improve blood perfusion also in the vicinity of the drug infused tissue region and by way of a further increase drug absorption rate into the circulation by increasing the available absorption volume. In some embodiments, the temperature profile can be applied to a region smaller than the drug infused tissue region to save battery life.

A device for heating the tissue region into which the drug is delivered according to some embodiments of the present invention is illustrated in FIG. 1. In this embodiment, the infusion catheter is combined with a heating element attached to the skin around the catheter. The treatment device is preferably a flat circular structure 7 with an opening in its center for the catheter tube 5 for entering the subcutaneous tissue. The other end of the catheter is connected to the drug delivery pump. In the illustrated embodiments, the treatment device includes a heating element 2, which may include a printed circuit board having the heating elements (e.g., resistors) provided thereon (as can be understood by one skilled in the art, other heating element types may be used). In some embodiments, the printed circuit board includes a temperature sensor 3. In some embodiments, a cooling element may be included in the case where more demanding temperature profiles are used.

The heating element can include a controller that controls the heating element (e.g., on/off or increased/decreased power) in order to stabilize the skin temperature to the required temperature according to the algorithm. In some embodiments, the temperature can be between 32-40° C. in order not to irritate the skin on the one hand and to have a sufficient effect on the tissue on the other hand. Temperature stabilization algorithms are well know in the art and can be executed by relatively simple controllers/processing units or ASICs. Skin or tissue damage depends on the applied temperature and the heat exposure time, so for a short period of few minutes even higher temperatures up to range of 42° C. can be used.

In some cases lower heating temperatures may be required. For instance, Novolog (aspart) insulin can be exposed to maximal limiting temperature of 37° C. (FDA document NDA 20-986/S-024, "NovoLog Insulin aspart (rDNA) Injection", Jul. 26, 2004). In such an embodiment, the skin temperature can be slightly higher as long as the immediate vicinity of the insulin infusion site is below 37° C. For this case, there is advantage in the heating configuration by the present invention and shown in FIG. 1, since the device warms the tissue and not the insulin, so minimal temperature modification is affecting the injected insulin per se while maximal heat stimulation is applied to the tissue, in order to increase local blood perfusion. Also as shown in FIG. 1, the heating element 2 is preferably not in contact with insulin infusion catheter 5. For this reason, the present invention suggests also thermal isolation 7 between insulin catheter 5 and heating element 2, such that the insulin is not overheated and minimally exposed to high temperatures.

In some embodiments, an additional or alternate temperature sensor 4 is located inside the catheter tube 5. This temperature sensor allows better control of the temperature of the drug infused tissue region. Specifically, first, the insulin limiting temperature inside the tissue can be avoided even though higher temperatures can be used at the skin to get optimal stimulation of the blood perfusion in the region. Also, by regulating the temperature inside the drug infused region to a fixed optimal temperature, a better stabilization of the drug chemical processes, pharmacokinetics, absorption into the blood system and/or pharmacodynamics can be achieved. The local temperature variations in the drug infused region induced by ambient temperature variations as well as other factors induce variations in the blood absorption rate of the drug and induces larger variability of the drug pharmacokinetics and pharmacodynamics. As mentioned before, in the case of insulin delivery, it is important to reduce the variability of the temporal profile of the insulin absorption into the blood and tighter local temperature control can be advantageous improve the glucose level regulation of diabetic patients.

In some embodiments, the heating element 2 and one or two of the optional temperature sensors 3 and 4 are connected to the drug delivery pump through cable 6. In this embodiment, the drug delivery pump may include the power source and the controller of the treatment process.

In some embodiments, element 7 covering heating element 2 is thermally isolating. Specifically, element 7 reduces the heat dissipation to the environment in case of heating the tissue. As mentioned earlier, element 7 can also thermally isolate the drug in catheter 5 from being exposed to the increased temperature of the heater(s). In case of cooling of the drug infused tissue region, element 7 reduces heat transfer from the environment to the cooled tissue region. It can also ease the thermal stabilization of the infused tissue region, in case of changing environments and ambient temperatures.

In some embodiments, the heating device as shown in FIG. 1 is attached to the tissue with an adhesive layer (tape) 1. The adhesive layer can also cover the heating element. In some embodiments, the adhesive layer may be a thermal conducting adhesive or a thin adhesive layer. The adhesive layer may be provided covered with a laminate (not shown in FIG. 1) that is peeled off by the user before insertion of the catheter and attachment of the heating device. Typically, for catheter insertion, the device is supplied with a sterile needle inside the catheter (not shown in the figure) that is pulled out after insertion of the catheter to the required tissue region.

In some embodiments, the heating device shown in FIG. 1 includes an adhesive thermally conducting layer in contact with the skin, an electrically isolating layer with temperature sensors, a heating layer, a thermally isolating layer and an adhesive layer for attaching heating device 2 to additional thermal isolation 7 if needed. All layers can be manufactured using printing techniques and mass production methods.

Figure 2:
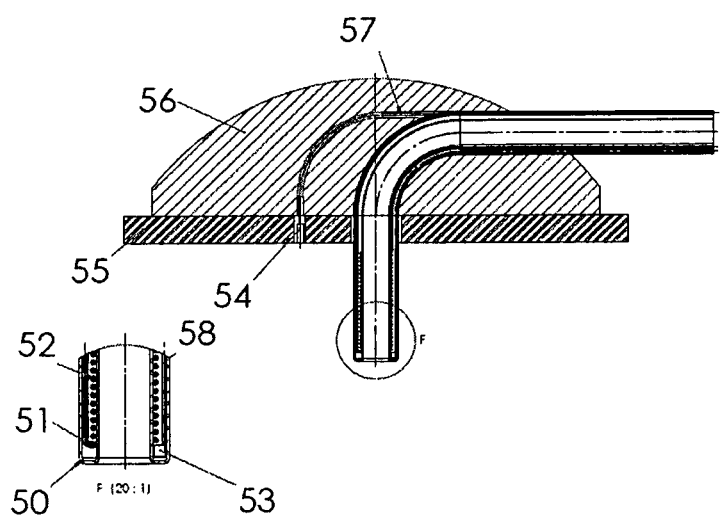
FIG. 2 illustrates an exemplary catheter for drug delivery combined with a heating element embedded into the catheter tube, according to some embodiments of the present invention.

Another optional device for heating the tissue region into which the drug is delivered is illustrated in FIG. 2. In this embodiment, the infusion catheter contains a heating element 52 in a distal part 50, which is close to the infused tissue region. The heating element can be made of a conductive wire with high enough resistance and good strength and durability. For instance, tungsten wires or deposition of thin copper strip are commonly used for this purpose. Heating element 52 may be embedded into the catheter tube during the manufacturing of the tube, using methods known in the art. For example, this can be done by wrapping the wire coil on a thin wall tube and then covering it with a second polymeric layer. The other side of the heating wire coil 51 is directed up in the tube as well. In some embodiments, the heating wire can be shaped in other forms such as a single loop or zigzag or whatever can be efficiently manufactured to provide the required heat for the infused tissue region. An advantage of heating inside the tissue is a smaller volume of tissue around the drug infused region is heated and hence requires less electric power. Also, the heated volume, usually in the subcutaneous tissue, is better isolated from the skin temperature which may vary with the ambient temperature. However, in this case, the catheter temperature can be limited to a temperature that will not alter the properties of the infused drug in case of drugs that are more sensitive to temperature increase then insulin. In the external heating configuration shown in FIG. 1, the spatial temperature distribution may be such that the skin temperature and tissue regions around but not close to the catheter tip are at higher temperature without causing any damage to temperature sensitive drugs. In the external heating configuration, the drug exposure to the higher temperatures may be more limited, although the high temperature still affects a portion of the drug infused tissue region or the tissue regions around the drug infused tissue regions.

In some embodiments, temperature sensor 53 is located inside the catheter tube as well. This sensor monitors the infused tissue region temperature. This temperature sensor allows better control of the temperature of the infused tissue region. By better stabilization of the drug chemical breakdown and dissolution processes or pharmacokinetics or absorption kinetics into the blood system an improved and more reproducible pharmacodynamic profile can be achieved. In this device, the controller can be either in the treatment device or in the drug delivery pump and controls the heating current to stabilize the infused tissue region temperature to the required temperatures and durations according to the algorithm.

In some embodiments, device element 56 that supports the catheter attachment to the body is thermally isolating to further reduce the power requirements of the heating element and by thus, battery weight. The heating device as shown in FIG. 2, is attached to the tissue with adhesive layer 55. The adhesive layer can come covered with a laminate (not shown in FIG. 2) that is peeled off by the user before insertion of the catheter and attachment of the heating device. In some embodiments, another temperature sensor 54 connected to sensor wire 57 may be in contact with the skin to improve the temperature stabilization algorithm. In some embodiments, only skin temperature is used in conjunction with the catheter heating element. In some embodiments, heating elements provided internally and externally of the tissue may be used.

The other side of the catheter is connected to the drug delivery pump. In some embodiments in this configuration as well as in other configurations detailed in the subject disclosure, all wires that connect the treatment device and the drug delivery pump may be embedded in the catheter tube connected to pump as shown in the tube cross section at FIG. 3. In some embodiments, the wires are attached to the outer side of the tube as shown in the cross-section illustrated in FIG. 4. Embedding or attaching the wires to the tube enables the device to be more comfortable for the user (e.g., to be worn and handled).

Figure 3:
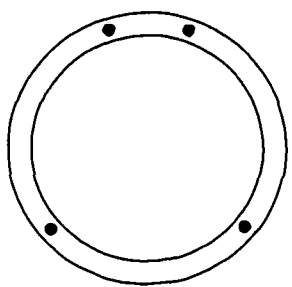
FIG. 3 illustrates an exemplary catheter for drug delivery combined with electric wires embedded into the catheter tube, according to some embodiments of the present invention.
Figure 4:
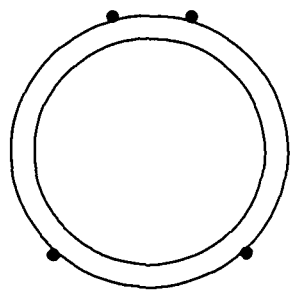
FIG. 4 illustrates an exemplary catheter for drug delivery combined with electric wires attached to the catheter tube, according to some embodiments of the present invention.

The wires shown in FIGS. 3 and 4 are preferable connected to the drug delivery pump. In some embodiments, two connectors may be used for connection of the disposable catheter and treatment device to the drug delivery pump. The first connector connects the catheter tube to the pump as currently established, for instance, in many current commercial insulin pumps. A second connector may be used to connect the wires used by the treatment device for communication between the pump unit and the treatment device unit or power supply or connecting sensors used for sensing of tissue parameters and/or infusion parameters to the pump unit. The wire connector can be one of the known connectors for connecting electrical wires. In case of using two separate connectors for the electrical wires and the infusion tube, the wires can also be separated from the tube.

Figure 5:
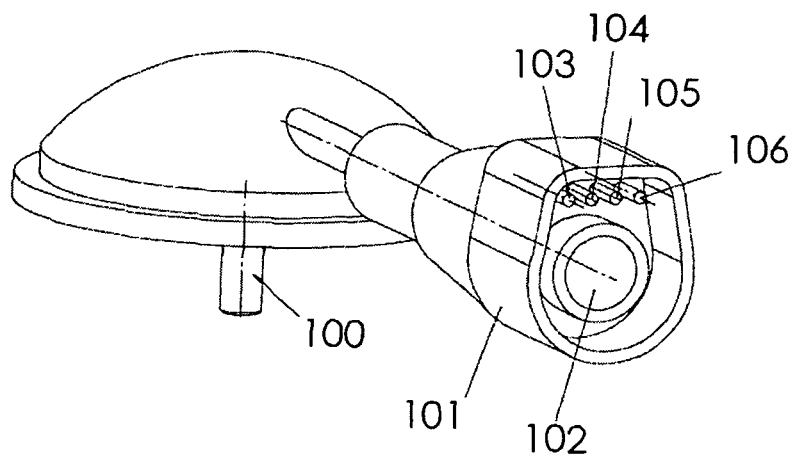
FIG. 5 illustrates an exemplary connector between a catheter for drug delivery and the drug delivery pump, where the connector connects the tube for the drug delivery as well as electric wires, according to some embodiments of the present invention.

In some embodiments, as shown in FIG. 5, the tube connector 102 and the electrical wires connectors 103-106 can be combined into a single housing 101. The single connector housing option is more comfortable for the user to handle, i.e., to assemble and disassemble the catheter and the treatment device 100 from the pump unit. The connector housing can also include a known prior art clip or locking mechanism that enables disconnection of the connector only when the locking mechanism is pressed or opened. Such locking mechanism can reduce also the chance of leakage of the infusion fluid from the connector.

In FIG. 5, four wires are used for controlling the treatment device by the pump unit and for connecting a sensor that measures the treatment level or effect in order to stabilize the treatment effect to the required level. In other cases of treatments, sensors and device configurations, a different number of wires may be connected through the connector.

In some embodiments, a similar connector can also be used on the treatment device's side. These embodiments may be more comfortable for the user in case of an infusion catheter and a drug delivery pump used for longer periods such as 2-3 days. For some time periods, the drug delivery pump can be detached from the user's body leaving a minimal weight and length of tubing in contact with the user's body. These embodiments can be useful and more comfortable for taking a shower. In such a case, the tubing and wires can include either a connector on both ends, a connector on the treatment device end only or a connector on the drug delivery pump device end only. In case of having a connector on the treatment device side, another alternative includes having a disposable tube connecting the treatment device and the drug delivery pump, where a reusable electrical cable is attached to the drug delivery pump and includes a connector for connecting to the treatment device. In some embodiments, the tube and wires may be disposable as with the catheter or its securing device, for instance, as the tube and catheter of common insulin infusion sets are designed.

Figure 6:
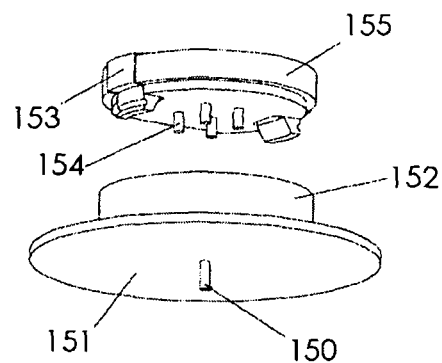
FIG. 6 illustrates an exemplary device for treatment of a tissue region combined with an infusion catheter made of disposable part and reusable part, according to some embodiments of the present invention.

In some embodiments, the treatment device can be made of two parts, one being disposable and one being reusable, as shown in FIG. 6. The disposable part includes the catheter 150 that is inserted into the tissue and the insertion mechanism (not shown in the figure). In some embodiments, the treatment device can also include the skin attachment part 151 and an adaptor mechanism 152 to connect the two parts. In some embodiments, the treatment device can include all or a portion of the treatment element such as the heating element (in the case of heat treatment or other elements for other tissue treatments or excitation methods of the present invention). In some embodiments, the treatment device may include one or more sensors.

The reusable part 155 may include all or a portion of the treatment element. It may include a processing unit, one or more sensors and a power source. The power source can be a rechargeable battery. As shown in FIG. 6, two parts are attached with a mechanical locking mechanism 153 and four pins 154 for electrical connections. In case of rechargeable battery, the user may have two alternating reusable units 155 whereas one is attached to the treatment device and one stays charging. When the battery in the treatment device is empty, damaged or the user is instructed (based on a specific battery schedule), the user switches between the two reusable units. The charger unit has the same mechanical and electrical connection as the disposable part 152 that easily fits the reusable unit 155.

In some embodiments, the reusable part communicates via a communication channel with the drug delivery pump, using wired, wireless, wireline or any other connection. In some embodiments, the treatment device has no communication with the drug delivery pump. For example, only the catheter tube, which is not shown in the FIG. 6, can be connected to the drug delivery pump.

Consequently, in the case of an insulin pump, this device can be used with many of the continuous subcutaneous insulin infusion pumps presently on the market and for those in development, for similar purposes. The treatment device identifies by itself the infusion of an insulin bolus and starts the treatment protocol accordingly. The beginning of insulin infusion can be identified as described earlier by a sensor in the treatment device such as an optical sensor on the transparent tube, a laser Doppler sensor, an ultrasonic Doppler sensor, a pressure sensor connected to the tube, or a conductivity sensor in the tube, optionally under applied magnetic field, or a temperature sensor of the infusion fluid in the tube. Alternatively, the treatment device can identify the pump motor electromagnetic emission or acoustic emission to detect the bolus period. The sensors that require contact with the infusion fluid, such as the conductivity sensor, are preferably located in the disposable part 152. The other sensors may be either in the disposable part or in the reusable part with a respective known in the art mechanical structure that allow them to measure the required infusion fluid parameter or parameters.

In some embodiments, a separate unit which is attached to the insulin pump detects the delivery of an insulin bolus and transmits the information to the treatment unit to start treatment, either with wired or wireless communication. The separate unit may sense the electromagnetic or acoustic emission of the pump motor or read the pump buttons when pressed or read the pump display or pump other indicators or have an additional button disposed on the pump for manual operation of the tissue treatment device. In some embodiments, the reusable unit may have at least one user input (e.g., a button) for the user to use (e.g., press) when the user desires the treatment to start.

In some embodiments the reusable part or the disposable part is connected with an electrical cable to a third unit that may include the power source, the control unit or other electronic parts of the device. In some embodiments, a single part disposable treatment device is electrically connected to the third unit.

Figure 7:
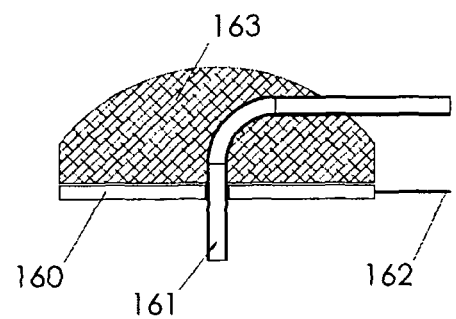
FIG. 7 illustrates an exemplary device for treatment of a tissue region combined with an infusion catheter made of disposable part and reusable part, according to some embodiments of the present invention.

An alternate embodiment of the present invention is illustrated in FIG. 7, where the reusable part is shaped as a thin disk 160 inserted between the disposable part 163 and the skin. Thin disk 160 can be a heater with a temperature sensor used to aid in stabilizing the temperature of the skin around the catheter insertion area. In some embodiments, the temperature sensor can be part of a thermostat that automatically regulates the heating temperature by connecting and disconnecting the heater element power lines, or other self regulating heaters, such as PTC thermistors, and or increasing or decreasing the power supplied to the heater.

In some embodiments, the thin heater can be manufactured by printing technologies. In some embodiments, the thin heater can be of thickness of 0.1-0.5 mm. In some embodiments, a thicker heater with thickness of 0.5-2 mm may be used. Also, a thin disk can be more flexible and more comfortable for the user. Before insertion of the catheter 161 into the tissue, the reusable disk 160 can be adhered or attached to the disposable part 163 such that the treatment element of the reusable device is adhered to the skin above the drug infused tissue region. In some embodiments, a special mechanical jig is used for attaching reusable disk 160 to disposable part 163. In some embodiments, an inserter, such as inserters used for insulin infusion sets, is used for entering both units to the tissue. The thin heater disk 160 and the catheter securing element 163 can be disposable. In some embodiments, thin heater disk 160 can fit several conventional catheter securing elements, including insulin conventional infusion sets.

The reusable treatment disk is connected to the drug delivery pump or to a third unit using a cable 162. The reusable treatment disk can perform many treatments or stimulations discussed in the present application, such as heating, massaging, vibrating, acoustic excitation, optical radiation, RF radiation, MW radiation, applying electrical field etc. In some embodiments, disposable part 163 can be wider than reusable part 160 such that the rims of the disposable part are used for attaching or securing the treatment device to the skin.

Figure 8:
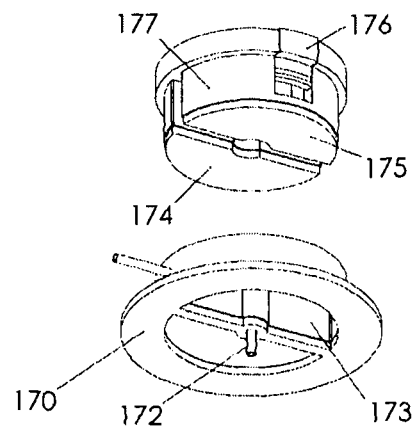
FIG. 8 illustrates an exemplary device for treatment of a tissue region combined with an infusion catheter made of disposable part and reusable part, according to some embodiments of the present invention.

FIG. 8 illustrates an alternate embodiment in which the disposable part 173 includes only the catheter tube 172, the insertion mechanism and the skin adhering element 170. Before insertion of the catheter into the tissue, the disposable part 173 can be attached to the reusable part 177 such that treatment elements 174 and 175 of the reusable part gets in contact with the skin when the treatment device is attached to the user's skin. In some embodiments, the disposable part 173 can be attached to the reusable part 177 with a locking mechanism 176. The reusable part 177 can be wired or wirelessly connected to the drug delivery pump or a third unit. Alternatively, it may not be connected to the drug delivery pump and thus, may include a power source, as described above. The reusable treatment part can perform treatments discussed above.

Figure 9:
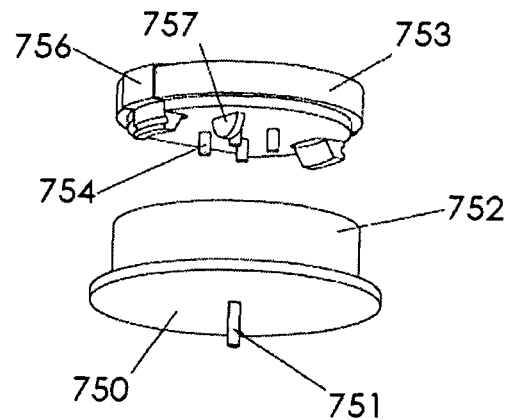
FIG. 9 illustrates an exemplary device for treatment of a tissue region combined with an infusion catheter made of disposable part and reusable part, according to some embodiments of the present invention.

FIG. 9 illustrates another embodiment in which the disposable part 752 includes the catheter tube 751, the insertion mechanism, the skin adhering element 750 the drug container and passive parts of the drug pump. In this embodiment, the reusable part includes a processing unit, a pump motor and may include some of the sensors, as described in shown in FIG. 6. The power source can be either in the reusable part or the disposable part. In case of using a rechargeable battery, the battery can be located in the reusable part, as discussed in FIG. 6. In some embodiments, the disposable battery is located in the disposable unit. Prior to insertion of the catheter into the tissue, the disposable part 752 may be attached to the reusable part 753 such that schematic electrical connection pins 754 fit the disposable part electrical connection pins and such that mechanical pump operating mechanism 757 in the reusable part fits the passive parts of the drug pump in the disposable unit. The pump mechanism can be one of the many known in the art pumping mechanisms. For instance, in case of a peristaltic pump, the mechanical pump operating mechanism 757 in the reusable part can be part of the pressure wheel of the peristaltic pump that presses a tube in the disposable part.

Alternately, a mechanical pump operating mechanism 757 in the reusable part can be a cog-wheel that rotates a matching pump cog wheel in the disposable part or moves a linear slider, such that the disposable unit includes only low cost parts. In some embodiments, some of the more expensive parts of the drug delivery pump can be included in the reusable unit. In some embodiments, the disposable part 752 is attached to the reusable part 753 with a locking mechanism 756. The reusable part 753 can be wirelessly or wired connected to the drug delivery pump or to a third unit or not connected and contain the power source as described before. The reusable treatment part can perform treatments discussed above.

Figure 10:
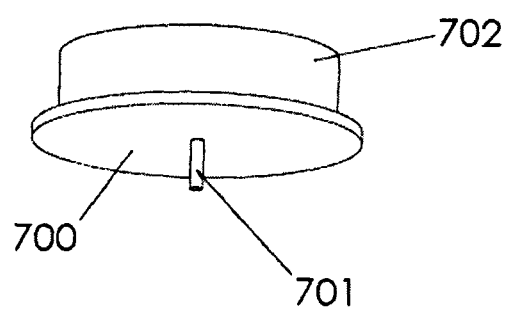
FIG. 10 illustrates an exemplary device for treatment of a tissue region combined with an infusion catheter and drug delivery pump, according to some embodiments of the present invention.

FIG. 10 illustrates an embodiment of the present invention, in which there is a single disposable unit 702 including the drug delivery pump, the treatment device, the catheter tube 701, the insertion mechanism, the skin adhering element 700 and the power source. The single unit pump and treatment device can perform the above described treatments. In some embodiments, in case of a single unit with a heat treatment that can be accomplished either by direct heating or by indirect heating such as a byproduct of radiation, the drug reservoir is thermally insulated from the heating element or from the heated regions. This is useful in the case of the insulin delivery because of insulin's sensitivity to high temperatures.

In some embodiments, the drug reservoir has in also a temperature sensor to verify that the drug temperature is not exceeding the limiting temperature. The same thermal insulation of the drug reservoir can be used in embodiments described above with reference to FIGS. 6-9.

The devices schematically shown in FIGS. 6-10 are examples of different combinations of disposable and reusable units that provide insulin delivery with treatment or excitation of the drug infused tissue region. As can be understood by one skilled in the art, other embodiments ranging from fully disposable units to fully reusable units (except the catheter that normally will be disposable) are also possible whereas each of the device components can be provided in the disposable or reusable units according to its way of implementation and its production cost.

In some embodiments, the third unit can be attached externally to the drug delivery device to improve user's comfort. In such a case, electrical wires can be attached to the catheter tube at a large portion of the catheter length and be separated only near the drug delivery device such that the drug catheter is connected to the drug delivery device and the wires are connected to the third unit. The third unit can include also power source and controller. When the drug delivery starts (e.g., drug bolus delivery), the third unit can detect operation of the drug-delivery device either actively by direct communication between the two units or by passively sensing some signals induced by drug delivery device when operated as described before, such as using the electromagnetic emission of the drug delivery device. In some embodiments, the third unit can be disposed in a bag, a pouch, a case, or a belt adaptor containing the drug delivery pump such as devices used for carrying insulin pumps. In such a case, the tube is connected to the insulin pump, while the wires are connected to the carrying device. The carrying device can also include a switch for manual start of the treatment or indicators for indicating that the treatment is applied or indicators that the battery power is adequate, too low or indicators that a problem occurred with the treatment, such as wire disconnection, etc. The switch or indicators, or a portion thereof, can be disposed also on the reusable unit or disposable unit or on the drug delivery pump.

In some embodiments, the devices by the present invention can have short range RF or IR communication with a data management and control unit, such as a Personal Digital Assistant ("PDA") computer, to a personal cellular phone or to an application specific data managing device that supports managing drug therapy. In case of insulin delivery, a data managing device can obtain glucose readings either from a glucose sensor manually, through data communication or by reading glucose sensing strips. The data managing device can get the information about previously consumed carbohydrates and other food or drinks. The data managing device can also retain patient history and relevant parameters, such as weight, BMI, insulin resistance etc.

The data managing device can also calculate the optimal required amount of insulin and the optimal tissue treatment or excitation profile. This information can be sent wirelessly to the drug delivery pump and to the treatment device, for optimal drug delivery. The treatment device may transmit tissue parameters measured by sensors disposed thereon to the data management unit (which may also be or include the control unit; "data management and control unit") as additional information for the therapy calculation or history for future statistics and data analysis. In some embodiments, the data management and control unit may only recommend to the user an optimal drug dosage, an optimal treatment and/or an excitation profile to be applied to the infused tissue region and the patient can approve the treatment before it starts. In some embodiments, the data management and control unit may recommend the user an optimal drug dosage only and the patient may approve the dosage before it starts and decide on best treatment or excitation to be applied to the infused tissue region. In some embodiments, the data management and control unit can be part of the drug delivery pump. In some embodiments, the data management and control unit can include a switch for manual start of the treatment, indicators for indicating that the treatment is applied, indicators that the battery power is adequate, too low or indicators for determining if a problem occurred with the treatment, such as wire disconnection, etc.

Figure 11:
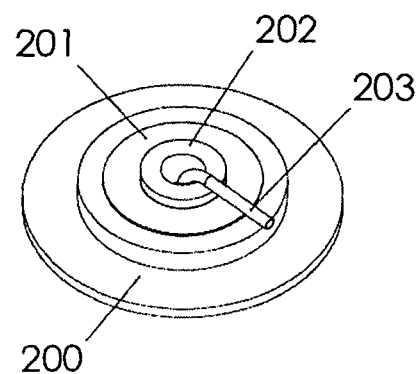
FIG. 11 illustrates an exemplary catheter for drug delivery combined with a mechanical vibrating element attached to the skin around the catheter, according to some embodiments of the present invention.
Figure 12:
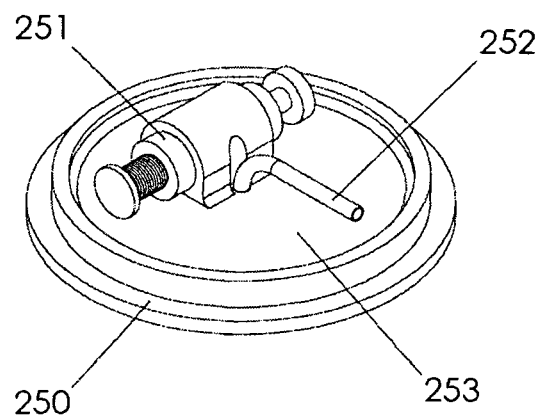
FIG. 12 illustrates an exemplary catheter for drug delivery combined with a mechanical vibrating element attached to the skin around the catheter, according to some embodiments of the present invention.

In some embodiments, tissue treatment or stimulation can include (either alone or in combination with other stimulation) vibrating the tissue region into which the drug is delivered. Two examples of such treatments devices are shown in FIGS. 11-12. The vibrating treatment device with open cover, shown in FIG. 11, includes, in combination with catheter securing element 200, an electric motor 202 that rotates a disk 201 with asymmetric load and tube 203. Rotating this disk causes the treatment device to vibrate in a circular vibration mode. By adhering the treatment device to the skin with an adhesive layer, the treatment device vibrates the tissue underneath the treatment device and the catheter tip. This vibration can have a frequency of about 1-50 Hz, which is commonly used for massaging tissue, an typically includes 60-300 rpm. As can be understood by one skilled in the art, other frequencies, or rotational velocities can be used as well. In some embodiments, the motor axis can be horizontal with the rotating disk vertical to the skin surface. In this case, the vibrations are vertical to the skin surface in addition to horizontal.

The vibrating treatment device with open cover, as shown in FIG. 12, includes, in combination with catheter securing element 250, an electromagnet 251 that pulls a ferromagnetic rod with two weights at either end thereof, and tube 252. A spring returns the rod to his initial location after the electromagnet is turned off. Thus, by applying a periodical signal to the electromagnet, the rod with its weights will vibrate at the periodic signal frequency and induce vibrations to the tissue underneath via surface 253. To improve vibration efficiency, the rod, weights mass and the spring force can be designed to have a mechanical resonance frequency at the required frequency for massaging the infused tissue.

When the resonance frequency is applied to the electromagnet a larger amplitude vibrations is induced. By adhering the treatment device to the skin with an adhesive layer, the treatment device vibrates the tissue underneath the treatment device and the catheter tip. In some embodiments, the vibration axis can be designed to vibrate to other directions, such as vertical or perpendicular to the skin surface. In some embodiments, the vibration device can vibrate mainly the catheter tip either horizontally or vertically using vibration mechanisms that induce excitation of the tissue near the catheter tip.

Figure 13:
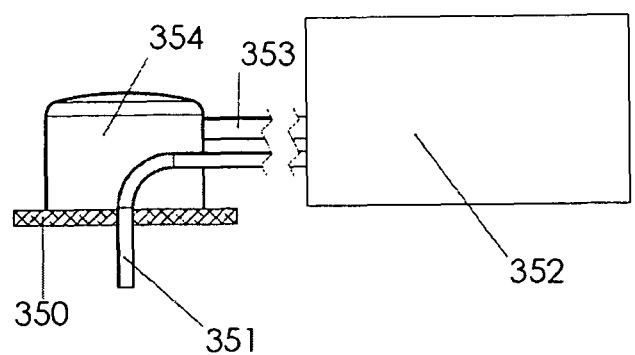
FIG. 13 illustrates an exemplary catheter for drug delivery combined with a massaging element that massages the skin around the catheter, using air cushion controlled by the drug delivery pump, according to some embodiments of the present invention.

An alternate embodiment of tissue massaging is illustrated in FIG. 13. This embodiment can massage with lower frequency and larger amplitude as compared to the vibrating embodiments. The treatment device (which in this embodiment may be disposable) includes a catheter tip 351 for inserting into tissue (as before), located in the middle of a chamber 354 with rigid wall all around except of the skin side, which also includes a flexible membrane 350. The flexible membrane is adhered to the skin as before with an adhesive layer, as part of the catheter insertion process described before, to secure the catheter in its position. Chamber 354 may be connected with additional tube 353 to the drug delivery pump 352. The tissue massaging is established by pumping air in and out of chamber 354 through tube 353 via an additional pump in the drug delivery pump unit, according to a treatment or massaging protocol. In this case, the control of the treatment protocol is accomplished by the drug delivery pump unit and the disposable unit can be relatively simple and low cost. When the air is pumped out of chamber 354, flexible membrane 350 curves into the chamber pulling the tissue adhered to it. When the air is pumped into the chamber, the flexible membrane curves out and pushes the tissue. This process is done periodically according to a typical frequency of about 0.01-10 Hz. Other frequencies are possible as well. In some embodiments, the chamber is filled with an incompressible fluid, such as water, and appropriate pump cause the fluid to flow in and out.

In an alternate embodiment, the flexible membrane can comprise a rigid surface which includes a plurality of openings and a flexible membrane covering the openings to improve adhesion to the skin, and to spatially modulate the skin massage. In yet another alternate embodiment, the flexible membrane outer surface can have small features (bumps) extending out of the surface to improve massaging effect to the tissue. In some embodiments, tube 353 can be connected to a third unit that controls and applies the massage treatment as described before.

Figure 14:
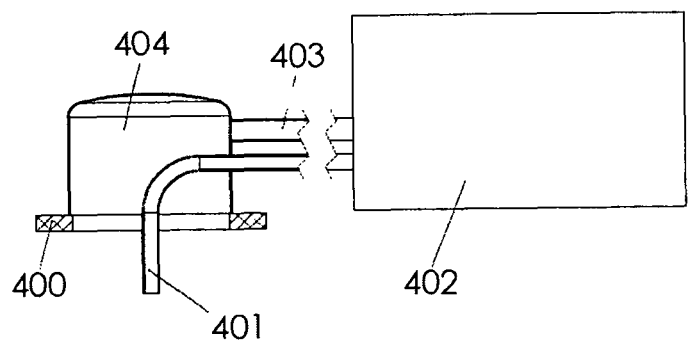
FIG. 14 illustrates an exemplary catheter for drug delivery combined with a suction element that affects the skin around the catheter, according to some embodiments of the present invention.

Another embodiment of a treatment device is a suction device that provides suction of the tissue around the infusion catheter, as shown in FIG. 14. Suction of a tissue region is known to improve blood perfusion in that tissue region. The treatment device (which is preferably disposable) includes a catheter tip 401 for insertion into the tissue (as before), located in the middle of a chamber 404 with rigid wall all around except of the skin side, where an opening is included. The chamber walls are adhered to the skin with a circular adhesive layer 400 that seals the chamber rim to the skin. The adhesive layer is attached to the skin during the catheter-insertion process to secure the catheter in its position. Chamber 404 is connected with an additional tube 403 to the drug delivery pump 402. The skin suction is accomplished by pumping the air out of chamber 404 through tube 403 via an additional pump provided in the drug delivery pump unit. In this case, the control of the treatment protocol is accomplished by the drug delivery pump unit and the disposable unit can be made simple and low cost. The suction is done according to a predetermined treatment protocol, for example—a suction of 1 minute in duration can be applied after an insulin bolus injection to improve insulin absorption into the blood system. Another example is applying vacuum in chamber 404 for 30 seconds and then releasing the vacuum for additional 30 seconds. This process can be repeated several times in order to increase blood perfusion in the tissue region underneath the treatment device. In some embodiments, the chamber opening to the tissue can be made of a rigid surface with few openings to increase adhesion area to the skin and to spatially modulate the skin suction. In some embodiments, tube 403 can be connected to a third unit that controls and applies the suction treatment as described before.

In some embodiment, in order to modify the delivered-drug's pharmacokinetic and/or pharmacodynamic profile, a small modulation of the infusion process through the infusion catheter is induced. In other words, the infusion fluid is slightly pulled in and out of the tissue during or after the drug infusion process. This action induces an increased flow of interstitial fluid ("ISF") around the catheter tip because of the variable induced pressure fields. The increased ISF flow increases the drug diffusion distance and reduces the time constant of the drug absorption into the blood system. The flow modulation can be done by the drug delivery pump by reversing the pump direction for short periods and small amount of pumped fluids. Also, the drug delivery pump can keep moving the infusion fluid in the catheter slightly in and out after the end of drug bolus infusion.

Figure 15:
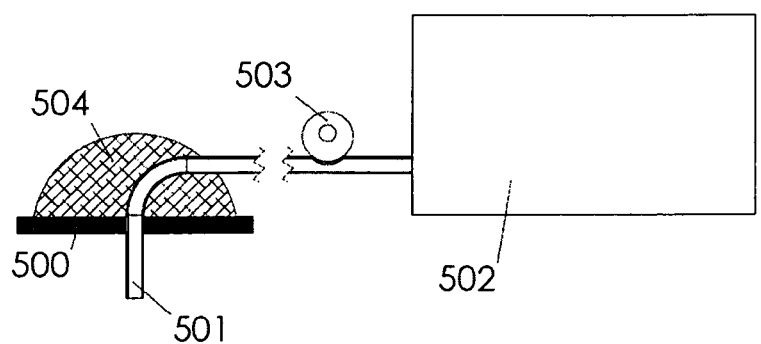
FIG. 15 illustrates an exemplary catheter for drug delivery with additional pumping element that move the infusion fluid in and out of the catheter, according to some embodiments of the present invention.
Figure 16:
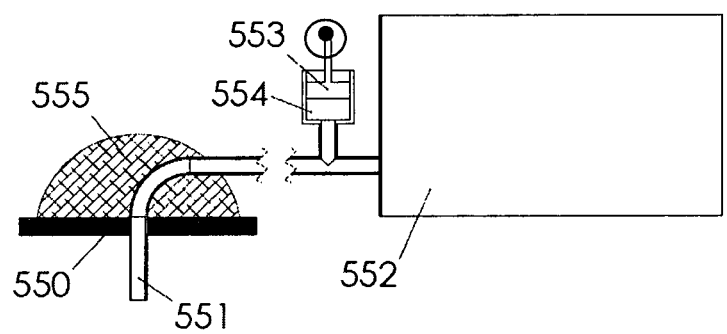
FIG. 16 illustrates an exemplary catheter for drug delivery with additional pumping element that move the infusion fluid in and out of the catheter, according to some embodiments of the present invention.

FIGS. 15-16 illustrate two exemplary embodiments of methods to implement the above tissue treatment with catheter units 504 and 555, respectively (each having skin adhering elements 500 and 550, respectively), as an additive component to existing drug delivery pumps 502, 552, without reversing the drug delivery pump direction. These embodiments include modulating the flow of the infusion fluid in the infusion catheter tube by two different modalities. In FIG. 15, a wheel 503 is provided having its rotating axis off the wheel center. Thus, when the axis is rotating, one side of the wheel applies pressure to the proximal side of tube 501 and pushes the infusion fluid forward. The other side of the wheel 503 releases the 501 and retracts the infusion fluid a slightly backwards. In FIG. 16, the fluid 554 modulation is done by a piston 553 connected to the catheter tube 551 and moves up and down to induce in and out flow to the infusion fluid in the catheter tube 551. In some embodiments, a proper air removal procedure and means should be used when the catheter is connected to the drug delivery pump 502, 552 and before insertion (preferably). In both embodiments, the modulation mechanism can be attached to the drug delivery pump, provided therein, in the disposable part or in a third unit connected to the infusion tube.

Figure 17:
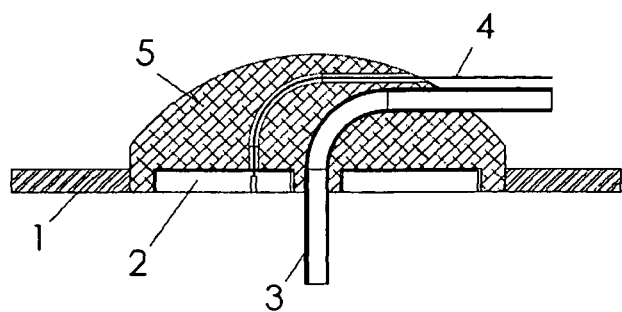
FIG. 17 illustrates an exemplary catheter for drug delivery with an acoustic excitation of the skin close to the catheter, according to some embodiments of the present invention.

In some embodiments, the tissue treatment device can include an acoustic excitation element to stimulate the vicinity of the tissue region into which the drug is delivered, as illustrated in FIG. 17. In these embodiments, the infusion catheter is preferably combined with the acoustic excitation element 2 attached to the skin around the catheter. The treatment device may comprise a flat circular structure 5 with a center opening for the catheter tube 3 that enters the subcutaneous tissue. The other side of the catheter may be connected to the drug delivery pump. The acoustic excitation element can be made of piezoelectric materials such as PZT or PVDF. The acoustic excitation can include low or high acoustical frequencies or higher frequencies in the ultrasonic region.

The acoustic excitation device is preferably attached to the tissue with an adhesive layer. The adhesive layer can be either on the outer ring area 1 or cover also the acoustic excitation element with an acoustic conducting adhesive, such as adhesive hydrogels. The acoustic excitation element can also be covered with an acoustic conducting layer such as acoustic hydrogel or liquid. The adhesive layer may be provided covered with a laminate (not shown in FIG. 17) that can be peeled off by the user before insertion of the catheter and attachment of the acoustic excitation device. Usually, for the catheter insertion, the device is supplied with a sterile needle inside the catheter (not shown in FIG. 17) that is pulled out after insertion of the catheter. The acoustic excitation element can be either connected to the drug delivery pump using cable 4 or to a third unit or to an electronics disposed as part of the acoustic excitation treatment device, as described earlier.

Figure 18:
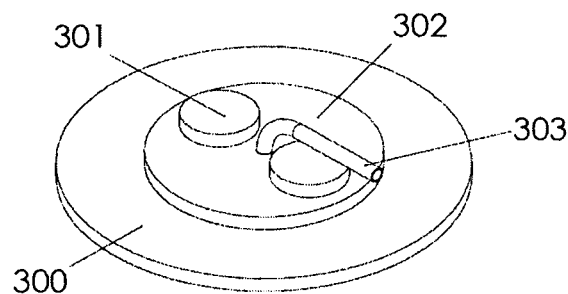
FIG. 18 illustrates an exemplary catheter for drug delivery combined with an optical radiation source irradiating the skin close to the catheter, according to some embodiments of the present invention.

In some embodiments, the tissue treatment device can use optical radiation to stimulate the tissue region, as illustrated in FIG. 18. In these embodiments, the infusion catheter is preferably combined with an optical radiation element 301 attached to the skin, via element 300, around the catheter. The treatment device may be a flat circular structure 302 with a central opening for the catheter tube 303 that enters the subcutaneous tissue. The other end of the catheter 303 is connected to the drug delivery pump. The optical radiation element can be made of known in the art light sources, such as LEDs, laser diodes, lamps, etc. The optical radiation can be in the visible or NIR or MIR regions. The light source may emit pulsed light or CW light and the pulsed light source may further emit pulses that are appropriate to generate photoacoustic or thermoacoustic signals on the catheter and/or in the tissue region close to the catheter. The optical radiation device is attached to the tissue with adhesive layer.

The adhesive layer can be provided on the outer ring area 301 or cover the optical radiation element with an optically transparent in the relevant optical wavelengths adhesive. The adhesive layer is covered with a laminate (not shown in FIG. 18) that is peeled off by the user before insertion of the catheter and attachment of the optical radiation device. Usually, for catheter insertion, the device is supplied with a sterile needle inside the catheter (not shown in the figure) that is pulled out after insertion of the catheter. In some embodiments, the light source can be disposed in the drug delivery device and delivered with an optical fiber or several fibers to the optical radiation treatment device. The optical radiation source can be either connected to the drug delivery pump using a cable, connected to a third unit or to an electronics disposed as part of the optical radiation treatment device, as described earlier.

Figure 19:
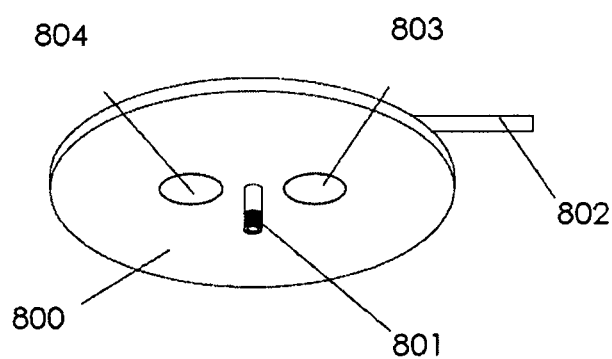
FIG. 19 illustrates an exemplary catheter for drug delivery combined with an optical radiation source irradiating the skin close to the catheter, according to some embodiments of the present invention.

In an alternate embodiment, optical radiation tissue excitation device, as illustrated in FIG. 19, coats the catheter tip with an optical absorption coating 801 that absorbs the wavelength or some of the wavelengths of the optical radiation. The treatment device can be similar to the optical radiation treatment device described before. In this embodiment, the treatment device can be a flat circular structure 800 with a central opening for catheter tube 801 to enter the subcutaneous tissue. The other end of the catheter 802 is connected to the drug delivery pump. The treatment device may also includes optical irradiation elements schematically shown by 803 and 804. The optical irradiation elements can be made of known in the art light sources, such as LEDs, laser diodes, lamps, etc. The light source may emit pulsed light or CW light and the pulsed light source may further emit pulses that are appropriate to generate photoacoustic or thermoacoustic signals on the catheter tip 801.

The optical irradiation wavelength can be either in the visible region or in the NIR. In some embodiments, using wavelengths range of 700-1000 nm provides relatively low absorption of the optical radiation in the tissue. Consequently, a larger portion of the illuminated radiation can be scattered in the tissue and absorbed in the catheter tip. The tip-absorbed optical radiation can induce a local hit around the catheter tip and efficiently heats the infused tissue region, as discussed above in FIG. 2. Using shorter wavelengths in the visible region, but also in the 700-1000 nm region, can increase the portion of the radiation absorbed by the hemoglobin and consequently can heat more blood or hemoglobin reach regions in the irradiated tissue region. Using longer wavelengths in the NIR, MIR or FIR regions can increase the portion of the radiation absorbed by the water in the tissue and consequently can heat more of the water to reach regions in the irradiated tissue region. Also, in case of using light pulses to create photoacoustic excitation, the portion of excitation induced at the catheter tip, hemoglobin regions or water regions, such excitation can be according to the absorbed radiation distribution and the photoacoustic coefficient of each region. The produced photoacoustic signal can be measured using an acoustic sensor disposed skin attachment structure 800 and can be used for monitoring the energy absorbed in each of those regions or catheter tip 801.

In some embodiments, some of the wavelengths of the above mentioned regions can be used for better control of the heated or stimulated region of interest. In some embodiments, at least one of the wavelengths is absorbed by a catheter tip coating and at least one wavelength is not absorbed by the coating to better control of the heated or stimulated region. The algorithm to control tissue excitation can obtain information from tissue temperature sensors (disclosed above), acoustic sensor, optical sensor, the drug delivery profile and additional drug or tissue parameters. The algorithm can control wavelengths to regulate the drug absorption into the blood system.

In some embodiments, a device similar to the one illustrated in FIGS. 2 and 18 can irradiate the drug infused tissue region, externally or internally, respectively, with radio frequency (RF) radiation or microwave (MW) radiation. Another optional embodiment can apply an electric field to the drug infused tissue region using, for instance, 2 electrodes similar to items 301 shown in FIG. 18, to apply the field to the skin or using electrodes disposed on the external side of the catheter tip inserted into the tissue. Also, the same device can be used to apply high or low frequency fields and even DC field. To improve the electrical contact the adhesive layer can be a conducting hydrogel or other known in the art materials to attach electrodes.

In some embodiments, an additional substance can be infused into the vicinity of the drug infused region, such that the additional substance modifies the drug pharmacokinetic and/or pharmacodynamic profile with or without the creation of a chemical or other reaction between the two substances. Specifically, the additional drug may influence either or both of the drug infused tissue region or improving the drug's pharmacokinetics and/or pharmacodynamics profiles. This effect is not necessarily due to a chemical reaction between the drug and the additional substance. In some embodiments, the additional substance improves local blood's perfusion in the vicinity of the drug infused region and accordingly, reduces the absorption time constant of the drug into the blood system. This effect may be additive or synergistic to the above described forms of stimulation. For instance, nitroprusside, which induces vasodilatation, can improve blood's perfusion in the drug infused tissue and improve the drug absorption into the blood system.

Figure 20:
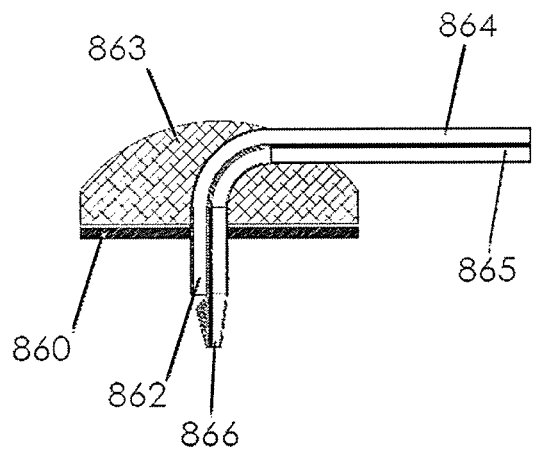
FIG. 20 illustrates an exemplary double lumen catheter for drug delivery, according to some embodiments of the present invention.

The additional substance can be infused into the drug infused region either through the same catheter or through an additional catheter, which can be attached or separated from the drug infusing catheter. In some embodiments, the catheter can be a double-lumen catheter with 2 openings inside the same tissue region or at two separate tissue regions, as shown in FIG. 20. Openings 866 and 862 of the two lumens 865 and 864, respectively, can be at different depths in the tissue. In the illustrated embodiment, the double lumen catheter is secured to the skin with a circular element 863 and an adhesive layer 860. In some embodiments, the catheter can include an additional treatment element, as discussed above, such that the combination of the additional substance and the treatment provides the desired tissue stimulation or treatment. In an embodiment of a single-lumen catheter, the additional substance can be either mixed with the drug and delivered, pumped, infused, or injected together into the catheter tube. Alternatively, the additional drug can come from a different container with a separate pump or drug delivery device and mixed in the catheter tube according to the flow rates of the drug and the additional substance using an infusion algorithm of the two substances. In some embodiments, the two containers can be either disposed in the same housing, attached to each other or separated. Similarly, in case of double lumen tube, one lumen may be connected to the drug delivery device and the second lumen may be connected to the additional substance delivery device. In some embodiments, a combination of the above treatment methods and/or devices can be placed into a single device to improve its operation and efficacy.

In some embodiments, the catheter can be drawn at a 90° penetration angle. As can be understood, other angles are possible. Smaller angles can improve attachment of the catheter, but insertion at such angles may be more irritating to the patient.

In some embodiments, a sensor can be added to the treatment device configuration. Alternatively, it can be added to general infusion sets, such as insulin infusion sets, and can be used to aid in detecting if the catheter securing element is lifted or starting to peel off the skin. The sensor can be provided in the catheter securing element so that it is in direct contact with the skin, indirect contact through the adhesive layer or other layers attached to the skin. The sensor can measure pressure or skin conductivity, impedance, and/or back-reflected optical or acoustic signal from the skin. A change of the contact level between the sensor and the skin will induce an electronic signal to either the treatment device or drug delivery device. Then, the device can either inform the user to fix the attachment of the securing element to the skin or to reinsert the catheter into the tissue in case it is detached or to pause or stop the drug delivery or the treatment till the catheter positioning is fixed.

In some embodiments, the treatment device can be secured to the patient using a strap or a belt that holds the treatment device into its position. The strap can be placed around any part of the patient's body, depending on the location of the drug infused region and the patient's comfort. Using such a strap can reduce the chances of the catheter to be pulled out in more demanding situations, such as jogging. For example, the strap can be placed around the abdomen, leg, thigh, arm etc. In some embodiments, the strap can have a compartment, a pocket or an adaptor for holding the drug delivery device. In embodiments using a third unit that supports the treatment device, the third unit can be attached to the strap or even be embedded into the strap. The third unit can be embedded into the strap or belt, and may be connected to the catheter disposable unit by electrical wires using a connector at the wire end. In some embodiments, the drug delivery pump can be attached to the strap and connected to the catheter disposable unit with a tube for drug delivery. In some embodiments, the disposable unit can be attached to the strap to further reduce chances of the catheter being pulled in more demanding situations.

The power source can be a thin battery, such as the batteries manufactured by Power Paper Ltd. The electronics can be implemented on a flexible printed circuit known in the art to provide the required flexibility for the patient's comfort.

Figure 21:
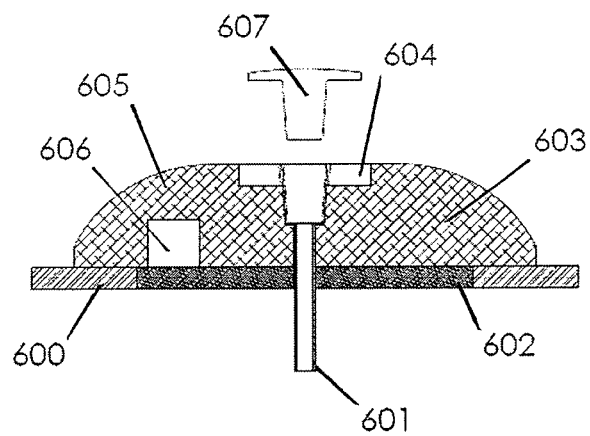
FIG. 21 illustrates an exemplary catheter for drug delivery combined with a port for syringe insertion, according to some embodiments of the present invention.

As can be understood by one skilled in the art, the above methods and devices for exciting the tissue are not limited to drug-delivery pumps and can be used with manual delivery of a drug, such as connecting a syringe (instead of a pump) to the proximal part of the catheter 601. In these embodiments, the catheter proximal part can end in a connector or a port that fits the syringe tip. Accordingly, the distal part of the catheter is inserted into the tissue as before. In some embodiments, the proximal part of the catheter tube is short, such as it is embedded into the treatment device 605, as shown in FIG. 21. In this case, treatment hardware, which includes treatment element 602, processor 606, power source and the abovementioned elements for tissue treatment or excitation, are disposed in the disposable catheter unit 603, which includes the adhesive layer 600 for skin attachment and the catheter distal tip 601. The syringe device can be either a regular syringe, an automatic syringe or other automated subcutaneous drug delivery devices that can provide a known volume of drug and can be connected to the catheter port for the drug delivery.

In some embodiments, the catheter unit with syringe port can be divided into disposable part and reusable part. In some embodiments, the syringe port comes with a plug 607 that covers the syringe port when not in use. In this case, there is no drug delivery unit in the system, the treatment device can detect infusion of the drug and start the treatment accordingly. The drug infusion can be detected using the above mentioned methods, such as flow detection, pressure detection, conductivity detection or temperature detection. In some embodiments, a mechanical pressure sensor 604, shown in FIG. 20, can detect the insertion of the syringe into the port automatically, manually via a switch on the treatment device or wirelessly by a remote control. The injection detection sensor can be also an optical or RF vicinity sensor that detects a unique RF transmission from the syringe unit or a unique optical pattern or signal. The injection sensor can also get some information from the injection device by either RF communication or optical reader such as barcode reader. The information can include the drug type and dose. In some embodiments, the treatment device includes a processing unit 606 that can get that information and fit the treatment algorithm accordingly, as described before. The same treatment device with syringe port can be used for several injections according to each treatment profile and duration, battery capacity and other parameters.

Figure 22:
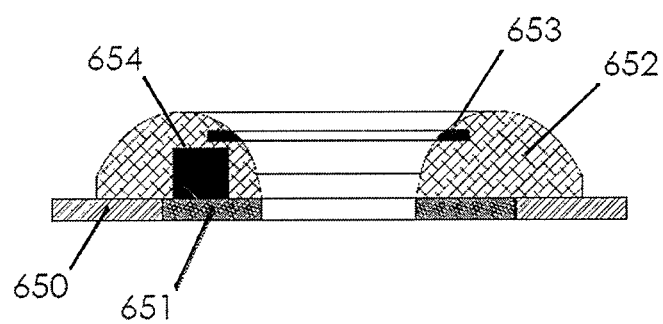
FIG. 22 illustrates an exemplary device for excitation of the skin and a tissue region underneath to which a drug is injected, according to some embodiments of the present invention.

In some embodiments, tissue or skin treatments or stimulation methods can be used to treat or excite a tissue region to which a drug is injected. In this case, as shown in FIG. 22, the excitation device 652 is attached to the skin and has a circular opening for direct drug delivery with a syringe and a needle. This option can fit injection devices without a needle, such as jet injectors or tissue perforation technologies or alternatively micro-needles injection devices. Also, the injection syringe can have many forms for drug injection in addition to the standard syringe, such as automatic syringes etc. An advantage of the device is that it is attached to the tissue prior to the drug injection. The device stimulates the injected tissue region after the drug delivery process in order to improve the drug absorption into the blood system. The excitation profile and duration is accomplished according to an algorithm that fits the drug and possibly the patient, as described earlier.

The detection of the injection can be done automatically by injection sensor 653, manually via a switch on the treatment device, or wirelessly by a remote control. The injection detection sensor can be an optical sensor or an RF vicinity sensor. The injection sensor can receive information from the injection device by either RF communication or optical reader such as barcode reader. The information can include the drug type and dose. In some embodiments, the treatment device includes a controller or processing unit 654 that can get that information and fit the treatment algorithm accordingly. The treatment element 651, as shown in FIG. 22, is placed around the injection area and the adhesive part 650, which attaches the device to the skin around it. In some embodiments, other shapes are possible, such as many of the shapes described before.

The same treatment device can be used for several injections according to each treatment profile and duration battery capacity and other parameters. Before injection, the skin in the device opening can be cleaned with cleaning fluid or pad such as alcohol pad through the device opening to prevent infections. In some embodiments, treatment device can have a U-shape to facilitate skin cleaning or other shapes.

Figure 23:
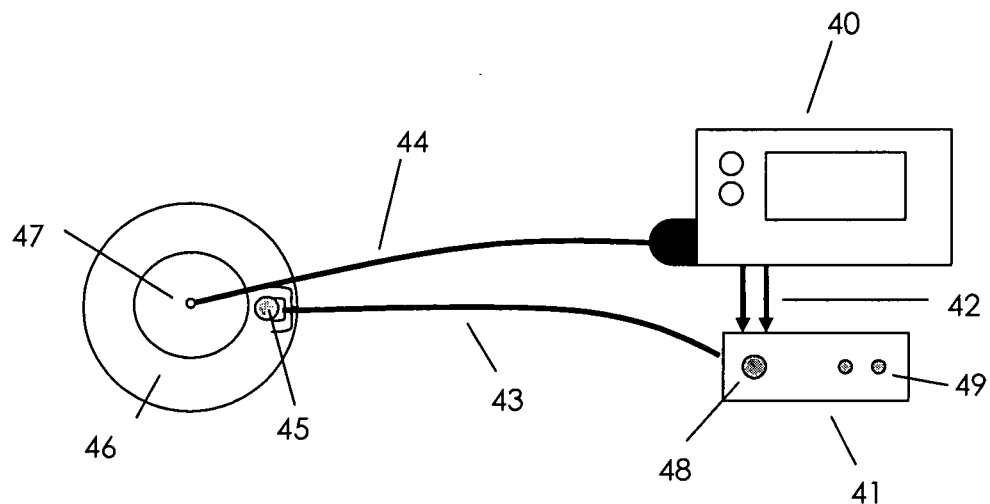
FIG. 23 illustrates an exemplary device for improving insulin pharmacodynamics, according to some embodiments of the present invention.

The following example demonstrates a device that improves the functionality of existing pump-based insulin-delivery systems. Such system, shown in FIG. 23, includes an insulin pump 40 and an infusion-set 44 which delivers the pumped insulin into the tissue. The infusion set comprises a tube 44 and a catheter 47, which is inserted into the subcutaneous tissue. The device has two components: i) a flat heater 46, which is attached to skin around the insertion point of the catheter, and ii) a controller unit 41, which is disposed into the casing of the insulin pump unit. The controller unit has a switch/button 48 for manual operation and two indicators 49 for "treatment is on" and for battery status. The two components are connected by wires 43.

The controller monitors the activity of the insulin pump using an electronic sensing element and it also controls the activity of the heating element. The controller monitors the electromagnetic emission from the pump. During a bolus mode, the pump emits a well defined series of electromagnetic pulses at constant rate, shown as arrows 42. For example during a bolus dose, the paradigm 722 insulin pump from Minimed emits specific pattern of electromagnetic pulses for each 0.1 unit of injected insulin at a rate of 0.1 unit per second. Counting those electromagnetic pulses enables one to determine the amount of injected insulin in the bolus initiate the operation of the heating element and adjust its parameters, such as the duration and heating temperature, accordingly. The temperature of the heater is controlled by the controller using a temperature sensor 45 located on the heating element. In this example the temperature of the heating element did not exceed 39° C. to avoid damage to the infused insulin.

In some embodiments, the heating device can be operated manually. In this case, the controller controls the activity of the treatment element. Once a user injects a bolus of insulin using the insulin pump, the user also activates a switch/button 48 located on the controller to initiate the heating-element operation for a predetermined duration. The temperature of the heater is controlled by the controller using a temperature sensor located within the treatment element (heating element). In this example the temperature of the heating element does not exceed 39° C. to avoid damage to the infused insulin.

The flat heating element used in this example has several layers. The upper layer is a polyethylene layer which seals the element. Below that layer, there is an etched circuit, below which there is a copper layer for heat distribution and mechanical support. Below that layer, there is another sealing polyethylene layer, below which there is an adhesive tape from 3M® which is bio-compatible. The heater has a thickness of less than 0.2 mm and his diameter is 3 cm. Thin electric wires of length of 60 cm with small connectors at both ends connected the heater to the controller unit. The power used for the heating can be 2 Watts. The heating was turned on and off by the controller to stabilize the skin temperature at 39° C. The heat duration was set to 30 minutes, after which the temperature regulation was stopped.

In general, the attachment and operation of the insulin delivery system with the heater is very similar to the operation of the insulin delivery system without the heater. The described device includes a case into which the insulin pump is inserted. The case contains also an electronic circuit and batteries to operate the controller and heater. Accordingly, the patient first connects the infusion set tube to the insulin pump. Then, the patient connects the electric wires connector to the electric connector on the heater. The patient then attaches the heater to the center of the catheter securing element using the adhesive tape of the catheter securing element. The insulin catheter is then inserted to the subcutaneous tissue either manually or using the catheter spring inserter. The mechanism of the catheter insertion is the same as usual using the same insertion module and following the same steps. The heater can be attached to the catheter securing element before insertion. The patient can connect the infusion set tube to the catheter. The patient connects the wires coming from the heater to a designated connector on the controller. The operation of the bolus is either automatic or manual as described before.

Figure 24:
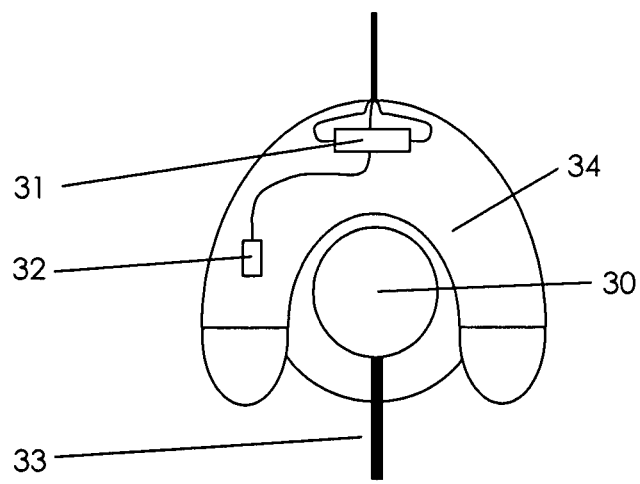
FIG. 24 illustrates an infusion catheter for insulin delivery with U shaped heater, according to some embodiments of the present invention

Another optional heater structure is shown in FIG. 24. In this case, the heater 34 is U shaped and attached to the skin around the insulin infusion set 30. The advantages of this configuration are that the heater can be an independent unit that fits many of the commercial infusion sets, which includes infusion set tubing 33, and also the thermal insulation between the insulin and the heater is kept. The U shaped heater can be thin or thicker and be built in many ways known in the art. The U shaped heater shown in FIG. 24 is made of heat conducting metal and has a resistor 31 for heating and a temperature sensor 32 for controlling the temperature.

In another optional heater structure, the heater is circular and attached to the insulin infusion set around the catheter prior to insertion into the body, as described above. The shape of cuts enable attachment of the heater to the infusion set prior to removing the catheter cover, although the catheter cover diameter may be larger then the central opening. It is important to remove the catheter cover or cup as the last operation before insertion of the catheter to the tissue because of safety and sterility issues. However, having the cuts of the heater enable using a heater with an optimized central opening diameter without the limitations of the catheter cover. This is important in order to optimally heat the drug infused tissue vicinity on one hand and keep the thermal insulation between the insulin in the catheter and the heater on the other hand. The heater can be an independent unit that fits many of the commercial infusion sets. The heater includes also a temperature sensor for controlling the temperature. The thickness of this heater may be about 0.2 mm.

To demonstrate the improvement of the insulin pharmacodynamics of the device described in this example, a euglycemic glucose clamp study was performed, using the following protocol. An insulin dependent diabetic volunteer treated with an insulin pump arrived after an overnight fast prior to taking a morning bolus with the pump. The subject lied down in supine position. The subject's blood glucose level was stabilized at 100 mg/dl. A bolus of insulin was given using the subject's insulin pump (0.15 U/kg). The pump was halted from the end of the bolus administration. A 20% dextrose drip was adjusted to keep the blood glucose level at about 100 mg/dl. Frequent blood sampling (every 5-10 min) was used for adjusting Glucose Infusion Rate (GIR) as required for tight control of the euglycemic glucose level.

Figure 25:
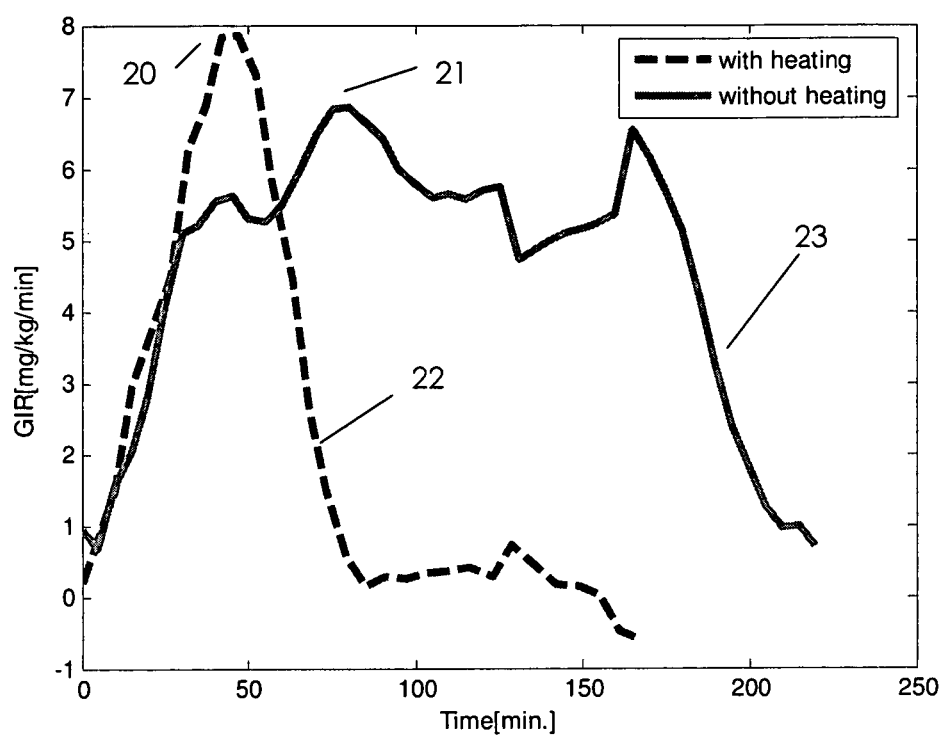
FIG. 25 illustrates an example of a graph of the insulin effect with and without treatment, according to some embodiments of the present invention.

The above described procedure was performed in the same subjects under the same conditions with and without using the heating device. A typical result is shown in FIG. 25. The two graphs show the GIR in glucose milligrams per minutes per subject's kg vs. time. The solid line shows the GIR without the heating treatment, while the dashed line shows the GIR on the same subject with heating. It can seen that the time to peak action was significantly shorten from 75 min without heating 21 to 50 min with heating 20. Also the GIR decrease, which is an indication for insulin clearance out of the circulation and cessation of it's systemic effects was much faster with heating 22 then without heating 23. Both of those parameters are important for better control of the glucose level since the delay of the peak action may cause glucose rise immediately following meals and the residual insulin level in the tissue and in the blood may induces late hypoglycemia and promote an error in the estimation of the effect of the next insulin bolus. Those two parameters (the delay to insulin peak action and the residual insulin level), which are important for tight glucose level regulation are very important also when automatically controlling the subcutaneous insulin infusion rate using a continuous glucose sensor and a control algorithm. There are many attempts to compose such an "artificial pancreas" since the development of continuous glucose monitors. In this case, any delay such as the current delays of the insulin absorption and action time, any variability in this delay and any variability in the residual insulin level in the body induces an error for the control algorithm that will result in less tight glucose regulation. Thus, another use of the methods and devices by the present invention is to combine them with a glucose sensor, insulin delivery device and a control algorithm to provide a better accuracy and robustness of a closed loop glucose level control system.

It should be noted that whenever the local effect of the treatment is described over the drug infused region, the treatment effect can be also on larger volume in the vicinity of the drug infused volume or on a smaller volume, depending on the specific treatment.

Although particular embodiments have been disclosed herein in detail, this has been done by way of example and for purposes of illustration only, and is not intended to be limiting. In particular, it is contemplated by the inventors that various substitutions, alterations, and modifications may be made without departing from the spirit and scope of the disclosed embodiments. Other aspects, advantages, and modifications are considered to be within the scope of the disclosed and claimed embodiments, as well as other inventions disclosed herein. The claims presented hereafter are merely representative of some of the embodiments of the inventions disclosed herein. Other, presently unclaimed embodiments and inventions are also contemplated. The inventors reserve the right to pursue such embodiments and inventions in later claims and/or later applications claiming common priority.

What is claimed is:

1. A system for delivery of a therapeutic first substance from a reservoir of a drug delivery pump to a body of a patient, comprising:
   a drug delivery pump comprising a reservoir to contain the therapeutic first substance;
   an infusion catheter configured to be inserted subcutaneously into a tissue of the patient at an insertion site, wherein a volume of tissue surrounding the insertion site comprises an infused region;
   a catheter securing element configured to be adhered to skin of the patient and further configured to secure the infusion catheter within the tissue of the patient;
   a tubing configured to transport the therapeutic first substance between the reservoir of the drug delivery pump and the infusion catheter; and
   a treatment element comprising a heater included with the catheter securing element and affixed thereto and configured to apply a treatment to a vicinity of the infused region to modify a pharmacodynamics profile of the therapeutic first substance,
   wherein
     the drug delivery pump is configured to infuse the therapeutic first substance into the infusion catheter for delivery to the infused region, and
     the heater is configured to heat the infused region without heating the reservoir and without heating any of the therapeutic first substance and the tubing above a predetermined limiting temperature above which degrades the therapeutic first substance prior to infusion of the therapeutic first substance into the infused region or prior to the therapeutic first substance being infused into the infusion catheter.

2. A system for delivery of a therapeutic first substance to a body of a patient, comprising:
   a drug delivery pump comprising a reservoir to contain the therapeutic first substance;
   an infusion set configured for use with and connection to the drug delivery pump, wherein the drug delivery pump provides a flow of the therapeutic first substance to the body of the patient, comprising:
     an infusion catheter configured to be inserted subcutaneously into a tissue of the patient at an insertion site, wherein a volume of tissue surrounding the insertion site comprises an infused region;
     a catheter securing element configured to be adhered to skin of the patient and further configured to secure the infusion catheter within the tissue of the patient;
     a tubing configured to transport the therapeutic first substance between the drug delivery pump and the infusion catheter;
     a treatment element comprising a heater and included with the catheter securing element and affixed thereto, and configured to apply a treatment to a vicinity of the infused region to modify a pharmacodynamic profile of the therapeutic first substance, and
     at least one wire provided along the tubing configured to supply at least one of power and control to the treatment element from a power source and/or a controller located adjacent or near the drug delivery pump and apart from the treatment element;
   wherein
     the drug delivery pump is configured to infuse the therapeutic first substance into the infusion catheter for delivery to the infused region, the heater is configured to heat the infused region without heating the reservoir and without heating any of the therapeutic first substance and the tubing above a predetermined limiting temperature above which degrades the therapeutic first substance prior to infusion of the therapeutic first substance into the infused region or prior to the therapeutic first substance being infused into the infusion catheter.

3. The system according to claim 2, wherein the treatment element power is regulated to produce a predetermined stable temperature at the infused region.

4. The system according to claim 3, treatment element is configured to be embedded into the catheter securing element, wherein the catheter securing element is configured to be connected to the drug delivery pump using the at least one wire and tubing.

5. The system according to claim 4, further comprising a connector housing configured to connect said at least one wire and tubing.

6. The system according to claim 5, wherein the connector housing is adjacent to the treatment element.

7. The system according to claim 5, wherein the connector housing is adjacent to the drug delivery pump.

8. The system according to claim 5, further comprising a cap configured to seal the connector housing when the connector housing is disconnected.

9. The system according to claim 3, further comprising a temperature sensor provided in the treatment element and wherein the at least one wire connects the temperature sensor to the drug delivery pump.

10. The system according to claim 2, wherein the treatment element is configured to apply a second treatment, wherein the second treatment comprises an energy source; and wherein the treatment is energy.

11. The system according to claim 10, wherein the energy is selected from a group consisting of: radiation, mechanical vibrations, suction, magnetic energy, ultrasound, light irradiation, RF irradiation, microwave, and electrical.

12. The system according to claim 11, wherein the drug delivery pump and the treatment element are configured to communicate with one another to determine when to apply the treatment and/or the second treatment.

13. The system according to claim 12, wherein communication between the drug delivery pump and the treatment element is wireless.

14. The system according to claim 10, wherein the drug delivery pump and the treatment element are configured to be combined in a single device.

15. The system according to claim 10, wherein the drug delivery pump includes a sensor for determining when to apply the therapeutic first substance.

16. The system according to claim 2, wherein the therapeutic first substance is insulin, insulin analogues or insulin mimetics.

17. The system according to claim 16, wherein the treatment is applied during and/or after an infusion of an insulin bolus dose.

18. The system according to claim 17, further comprising a processing unit configured to initiate the treatment element to apply the treatment upon detection of the insulin bolus.

19. The system according to claim 16, wherein the treatment is applied before, during and/or after an infusion of an insulin bolus dose.

20. The system according to claim 16, wherein the treatment element provides heat subsequent to an infusion of an insulin bolus dose for a period of between about 10 minutes and about 30 minutes.

21. The system according to claim 14, wherein the treatment element provides heat subsequent to an infusion of an insulin bolus dose for a period of between about 1 minutes and about 10 minutes.

22. The system according to claim 2, further comprising a processing unit for controlling at least the treatment element and optionally the drug delivery pump for delivering the therapeutic first substance to the infusion catheter.

23. The system according to claim 22, wherein the processing unit is disposed in the drug delivery pump.

24. The system according to claim 22, wherein the processing unit is disposed in an enclosure adjacent to the drug delivery pump.

25. The system according to claim 22, wherein the processing unit is disposed in an enclosure attached to the drug delivery pump.

26. The system according to claim 2, wherein the treatment element is configured to regulate heating of the infused region to stabilize a temperature of the therapeutic first substance infused in the tissue region at approximately the predetermined limiting temperature.

27. The system according to claim 26, wherein the predetermined limiting temperature is between about 37 degrees C. and about 42 degrees C.

28. The system according to claim 26, wherein the predetermined limiting temperature is between about 37 degrees C. and about 39 degrees C.

29. The system according to claim 26, wherein the predetermined limiting temperature is between about 32 degrees C. and about 37 degrees C.

30. The system according to claim 2, further comprising a temperature sensor configured to indicate a temperature of the therapeutic first substance prior to infusion into the infused region.

31. The system according to claim 30, further comprising a processing unit configured to verify that the therapeutic first substance is not heated above the predetermined limiting temperature prior to the therapeutic first substance being infused into the infused region.

32. The system according to claim 2, wherein the catheter securing element and treatment element are disposed in the same housing.

33. The system according to claim 32, wherein the catheter securing element is combined with treatment element in the same disposable housing.

34. The system according to claim 2, further comprising an activator for manual activation of said treatment element.

35. The system according to claim 34, wherein said communication channel comprises wireless communication.

36. The system according to claim 2, wherein the pharmacodynamic profile is modified either before, during and/or after a period of delivery of the therapeutic first substance to the patient.

37. The system according to claim 2, wherein the treatment element is further configured to modify absorption of the therapeutic first substance into at least one of the blood system and the lymphatic system of the patient during and/or following a period of delivery of the therapeutic first substance to the patient.

38. The system according to claim 2, wherein the tissue comprises a blood vessel.

39. The system according to claim 2, wherein the pharmacodynamic profile of the therapeutic first substance is modified to enable a faster onset of action of the therapeutic first substance infused into the infused region.

40. The system according to claim 2, wherein the treatment element includes a processing unit and wherein the drug delivery pump and the reservoir to contain the therapeutic first substance are provided in the same housing.

41. The system according to claim 2, wherein the heater is attached to skin around the insertion site.

42. The system according to claim 2, wherein the heater is attached to skin around the catheter securing element.

43. The system according to claim 2, wherein the heater is U shaped.

44. The system according to claim 2, wherein the heater does not heat the therapeutic first substance prior to the therapeutic first substance being infused into an end of the infusion catheter or prior to being infused into the infused region.

45. The system according to claim 2, further comprising thermal insulation disposed between the treatment element and the reservoir and wherein the thermal insulation is configured to prevent heating of the therapeutic first substance above the predetermined limiting temperature.

46. The system according to claim 2, wherein the predetermined limiting temperature is about 37 degrees C.

47. The system according to claim 2, wherein the treatment element is provided between the catheter securing element and the skin of the patient.

48. The system according to claim 2, wherein the treatment element comprises an intra catheter electrical heater.

49. The system according to claim 2, wherein the treatment element is configured to heat the infused region using optical radiation.

50. The system according to claim 2, further comprising a temperature sensor provided adjacent to the skin of the patient and proximal to the insertion site of the infusion catheter.

51. The system according to claim 2, further comprising a temperature sensor embedded into the infusion catheter and further configured to be proximal to the infused region.

52. The system according to claim 2, wherein heat is produced at a power of between about 0.25 watts and about 2 watts.

53. The system according to claim 2, wherein the treatment element operates between on and off states to produce a predetermined stable temperature at the infused region.

54. The system according to claim 2, wherein the catheter securing element is disposable and the treatment element is disposable.

55. The system according to claim 2, wherein the treatment element is configured to apply one or more additional substances to the infused region wherein a second substance modifies the pharmacodynamic profile of the therapeutic first substance.

56. The system according to claim 2, wherein the treatment element is configured to apply one or more additional substances to the infused region wherein a second substance modifies absorption of the therapeutic first substance into a blood system and/or lymphatic system of the patient and/or promotes clearance of therapeutic first substance from the infused region.

57. The system according to claim 2, further comprising a processing unit for controlling administration of the therapeutic first substance; and a communication channel for communication between said treatment element and the processing unit.

58. The system according to claim 2, wherein the system is configured to modify a bolus dose effect of the therapeutic first substance on the body of the patient.

59. The system according to claim 2, wherein the device further comprises a housing configured to include:
- the power source,
- the controller,
- at least one electrical contact,
- at least one indicator configured to indicate: whether the treatment is applied, whether the power source has adequate power, whether a problem occurred with the treatment, and/or whether the at least one electrical contact is disconnected,
- at least one activation switch configured to activate at least one component of the device, and
- another reservoir configured to contain a second substance.

60. The system according to claim 2, wherein the treatment element is configured to be combined with the catheter securing element and/or the drug delivery pump.

* * * * *